United States Patent
Hayashi et al.

(10) Patent No.: US 10,189,007 B2
(45) Date of Patent: Jan. 29, 2019

(54) METHOD FOR PRODUCING POROUS CELLULOSE BEADS AND ADSORBENT EMPLOYING SAME

(71) Applicant: KANEKA CORPORATION, Osaka-shi (JP)

(72) Inventors: Asuka Hayashi, Takasago (JP); Yoshikazu Kawai, Takasago (JP); Ken-ichiro Morio, Osaka (JP)

(73) Assignee: KANEKA CORPORATION, Osaka-shi (JP)

( * ) Notice: Subject to any disclaimer, the term of this patent is extended or adjusted under 35 U.S.C. 154(b) by 103 days.

(21) Appl. No.: 15/029,551

(22) PCT Filed: Oct. 14, 2014

(86) PCT No.: PCT/JP2014/077362
§ 371 (c)(1),
(2) Date: Apr. 14, 2016

(87) PCT Pub. No.: WO2015/056681
PCT Pub. Date: Apr. 23, 2015

(65) Prior Publication Data
US 2016/0243521 A1    Aug. 25, 2016

(30) Foreign Application Priority Data
Oct. 15, 2013    (JP) .................... 2013-215121

(51) Int. Cl.
*B01J 20/24*    (2006.01)
*C07K 17/12*    (2006.01)
(Continued)

(52) U.S. Cl.
CPC .............. *B01J 20/24* (2013.01); *B01J 20/285* (2013.01); *B01J 20/286* (2013.01); *B01J 20/305* (2013.01);
(Continued)

(58) Field of Classification Search
None
See application file for complete search history.

(56) References Cited

U.S. PATENT DOCUMENTS

| | | | |
|---|---|---|---|
| 4,634,470 A | 1/1987 | Kamide et al. | |
| 5,328,603 A * | 7/1994 | Velander | B01J 20/291 210/198.2 |

(Continued)

FOREIGN PATENT DOCUMENTS

| | | |
|---|---|---|
| CA | 2 828 369 A1 | 9/2012 |
| JP | H 3-252430 | 11/1991 |

(Continued)

OTHER PUBLICATIONS

Gericke et al. (Chemical Reviews, 2013, 113, 4812-4836).*

(Continued)

*Primary Examiner* — Clare M Perrin
(74) *Attorney, Agent, or Firm* — Oblon, McClelland, Maier & Neustadt, L.L.P.

(57) ABSTRACT

The objective of the present invention is to provide a method for easily and efficiently producing cellulose beads which have pore shape suitable for an adsorbent and of which adsorption performance is excellent without using highly toxic and highly corrosive auxiliary raw material and without industrially disadvantageous cumbersome step. The method for producing porous cellulose beads according to the present invention is characterized in comprising (a) the step of preparing a fine cellulose dispersion by mixing a low temperature alkaline aqueous solution and cellulose, (b) the step of preparing a mixed liquid by adding a crosslinking agent to the fine cellulose dispersion, (c) the step of preparing an emulsion by dispersing the mixed liquid in a disper- (Continued)

sion medium, (d) the step of contacting the emulsion with a coagulating solvent.

11 Claims, 14 Drawing Sheets

Specification includes a Sequence Listing.

(51) Int. Cl.
*B01J 20/285* (2006.01)
*B01J 20/30* (2006.01)
*B01J 20/32* (2006.01)
*B01J 20/286* (2006.01)
*C08J 9/28* (2006.01)
*C08B 15/10* (2006.01)
*C08J 9/16* (2006.01)
*C07K 1/14* (2006.01)
*C07K 1/22* (2006.01)

(52) U.S. Cl.
CPC ....... *B01J 20/3085* (2013.01); *B01J 20/3212* (2013.01); *B01J 20/3274* (2013.01); *C07K 17/12* (2013.01); *C08B 15/10* (2013.01); *C08J 9/28* (2013.01); *B01J 20/3217* (2013.01); *B01J 20/3293* (2013.01); *C07K 1/145* (2013.01); *C07K 1/22* (2013.01); *C08J 9/16* (2013.01); *C08J 2201/026* (2013.01); *C08J 2201/0547* (2013.01); *C08J 2301/00* (2013.01)

(56) References Cited

U.S. PATENT DOCUMENTS

| 5,410,034 | A  | 4/1995  | Isogai et al.   |
|-----------|----|---------|-----------------|
| 8,664,152 | B2 | 3/2014  | Umeda et al.    |
| 2003/0012941 | A1 | 1/2003  | Fujita et al.   |
| 2003/0186041 | A1 | 10/2003 | Fujita et al.   |
| 2008/0021365 | A1 | 1/2008  | Kobayashi et al.|
| 2008/0070027 | A1 | 3/2008  | Fujita et al.   |
| 2009/0062118 | A1 | 3/2009  | Umeda et al.    |
| 2013/0172538 | A1 | 7/2013  | Hirano et al.   |
| 2013/0331563 | A1 | 12/2013 | Kawai et al.    |
| 2014/0128253 | A1 | 5/2014  | Umeda et al.    |
| 2015/0297820 | A1 | 10/2015 | Kawai et al.    |
| 2016/0355662 | A1 | 12/2016 | Tokuoka et al.  |

FOREIGN PATENT DOCUMENTS

| JP | H 6-82435     | 3/1994  |
| JP | 9-124702 A    | 5/1997  |
| JP | 10-195103 A   | 7/1998  |
| JP | H 11-158202   | 6/1999  |
| JP | 2009-242770 A | 10/2009 |
| JP | 2010-236975   | 10/2010 |
| JP | 2010-236975 A | 10/2010 |
| WO | 2006/025371 A1 | 3/2006 |
| WO | 2012/033223 A1 | 3/2012 |
| WO | 2012/121258 A1 | 9/2012 |
| WO | WO 2014/038686 | 3/2014 |
| WO | WO 2015/137170 | 9/2015 |

OTHER PUBLICATIONS

Extended European Search Report dated Jul. 7, 2017 in Patent Application No. 14853802.8.
"Viskosität", Internet Citation, XP002261914, 2003, pp. 81-98 (with partial English translation).
International Search Report dated Jan. 20, 2015, in PCT/JP2014/077362 Filed Oct. 14, 2014.
Hershko, et al., "Removal of Pathogenic Autoantibodies by Immunoadsorption," Annals of the New York Academy of Sciences, 2005, vol. 1051 pp. 635-646.
Staudt, et al., "Immunoadsorption in a dilated cardiomyopathy: 6-month results from a randomized study," American Heart Journal, vol. 152, No. 4, 2006 (6 pages).
Kuga, "New Cellulose Gel for Chromatography," Journal of Chromatography, vol. 195, 1980 (6 pages).
Extended European Search Report dated Oct. 19, 2018, in European Patent Application No. 16780059.8 (8 pages).

* cited by examiner

METHOD FOR PRODUCING POROUS CELLULOSE BEADS AND ADSORBENT EMPLOYING SAME

TECHNICAL FIELD

The present invention relates to a method for producing porous cellulose beads.

BACKGROUND ART

Porous cellulose beads are safer than beads composed of a synthetic polymer, and the non-specific adsorption thereon is small. In addition, the mechanical strength of porous cellulose beads is high, and the beads have many hydroxy groups, which can be used for introducing a ligand capable of interacting with a target substance to be adsorbed. Accordingly, porous cellulose beads are used as a base material for various adsorbents such as an adsorbent for chromatography and an affinity adsorbent. Among the examples, an affinity adsorbent is used as a medical adsorbent and an adsorbent for purifying a medical antibody, since a target substance can be purified and an undesired substance amount can be reduced efficiently by using an affinity adsorbent. In particular, as a medical adsorbent for treating rheumatism, hemophilia or dilated cardiomyopathy, an adsorbent produced by immobilizing Protein A as an affinity ligand on a porous carrier has attracted attention (for example, Non-patent document 1 and Non-patent document 2).

In addition, it has attracted attention that an adsorbent produced by immobilizing Protein A as an affinity ligand on a porous carrier is used as an adsorbent for purifying an antibody pharmaceutical by specifically adsorbing an immune globulin, i.e. IgG.

Many methods for producing porous cellulose beads require a cumbersome step in comparison with the case of using a general synthetic polymer, since cellulose is considered to be hardly dissolved. As such a method, for example, Patent document 1 discloses a method in which cellulose is dissolved in a solvent such as calcium thiocyanate aqueous solution and coagulated. Such a solvent is highly corrosive and toxic, and it is difficult due to the solvent to design a plant. The cellulose solution used in the method exhibits peculiar behaviors, and the porous cellulose beads obtained by the method have considerably large pores and broad pore size distribution (for example, Non-patent document 3). When such porous cellulose beads obtained by the method are used for an adsorbent to adsorb an antibody and the like, high adsorption performance cannot be expected, since the specific surface area thereof is small. In addition, for example, Patent Document 2 discloses a method for producing a porous cellulose carrier by binding a substituent group to the hydroxy group of cellulose in order to improve the solubility of the cellulose, dissolving the cellulose in a general solvent to carry out agglomeration, and then removing the substituent group. However, the steps of the method are cumbersome and molecular weight may be decreased during the steps of reacting and removing the substituent group. Thus, the strength of the carrier tends to be not enough to be used in high-speed processing and large scale which have been recently required.

Furthermore, for example, Patent documents 3 and 4 disclose a method in which cellulose is dissolved in sodium hydroxide aqueous solution having low temperature. However, in the method described in Patent document 3, after the step of heating a mixture of cellulose and a hydrogen bond-cleaving solution at 100 to 350° C. under pressure, the mixture is dissolved in an alkaline aqueous solution. Such a step is industrially disadvantageous. In addition, the method described in Patent document 4 requires the steps in which cellulose is dispersed in a strong base solution, and the dispersion is once frozen and then melted.

Patent document 5 discloses the cellulose which can be dissolved in an alkaline solution. However, the cellulose is a micro fiber having a diameter of 1 μm or less, and further micronized to 500 nm or smaller. Such a micronizing procedure is not suitable for industrial production.

Very recently, Patent document 6 discloses a method in which microbial cellulose is dissolved in an alkaline solution to prepare a cellulose solution, the cellulose solution is particulated by adding a dispersion medium, and the microbial cellulose particle is freezed and then washed to obtain cellulose beads. However, the method is not suitable for an industrial production due to the cumbersome steps.

PRIOR ART DOCUMENT

Patent Document

Patent Document 1: JP 2009-242770 A
Patent Document 2: WO 2006/025371
Patent Document 3: U.S. Pat. No. 4,634,470 B
Patent Document 4: U.S. Pat. No. 5,410,034 B
Patent Document 5: JP H9-124702 A
Patent Document 6: JP 2010-236975 A

Non-Patent Document

Non-patent Document 1: Annals of the New York Academy of Sciences, 2005, Vol. 1051, p. 635-646
Non-patent Document 2: American Heart Journal, Vol. 152, Number 4, 2006, p. 712e1-712e6

DISCLOSURE OF THE INVENTION

Problems to be Solved by the Invention

The objective of the present invention is to provide a method for easily and efficiently producing cellulose beads which have pore shape and narrow pore size distribution suitable for an adsorbent and of which adsorption performance is excellent without using highly toxic and highly corrosive auxiliary raw material and without industrially disadvantageous cumbersome step.

Means for Solving the Problems

The inventors of the present invention made extensive studies to solve the above problems. As a result, the inventors completed the present invention by finding that porous cellulose beads of which adsorption performance is more excellent when a ligand is immobilized on the beads can be efficiently produced by mixing an alkaline aqueous solution having low temperature and a cellulose powder to prepare a fine cellulose dispersion and adding a crosslinking agent to the fine cellulose dispersion.

Hereinafter, the present invention is described.

[1] A method for producing porous cellulose beads, comprising
(a) the step of preparing a fine cellulose dispersion by mixing a low temperature alkaline aqueous solution and cellulose, (b) the step of preparing a mixed liquid by adding a crosslinking agent to the fine cellulose dispersion, (c) the step of preparing an emulsion by dispersing the mixed liquid in a dispersion medium, (d) the step of contacting the emulsion with a coagulating solvent.

[2] The production method according to the above [1], wherein a temperature of the alkaline aqueous solution in the step (a) is not less than 0° C. and not more than 25° C.

[3] The method for producing porous cellulose beads according to the above [1] or [2], wherein the crosslinking agent is an epoxy group-containing compound.

[4] The method for producing porous cellulose beads according to the above [3], wherein the epoxy group-containing compound is a glycidyl ether compound.

[5] The method for producing porous cellulose beads according to any one of the above [1] to [4], wherein a solubility of the crosslinking agent in water is not less than 50%.

[6] The method for producing porous cellulose beads according to any one of the above [1] to [5], wherein a viscosity of the crosslinking agent is not less than 100 mPa·s and not more than 50000 mPa·s.

[7] An adsorbent, obtained by immobilizing a ligand capable of interacting with a target substance on the beads produced by the method for producing porous cellulose beads according to any one of the above [1] to [6].

[8] An adsorbent, comprising the porous cellulose beads produced by the method according to any one of the above [1] to [6] and a ligand capable of interacting with a target substance.

[9] A method for producing an adsorbent, comprising the step of immobilizing a ligand capable of interacting with a target substance on the porous cellulose beads produced by the method according to any one of the above [1] to [6] in order to obtain the adsorbent.

[10] A purification method, comprising the step of using the adsorbent according to claim 7 or 8.

Effect of the Invention

According to the present invention, cellulose beads which have pore shape and narrow pore size distribution suitable for an adsorbent and of which adsorption performance is excellent can be easily and efficiently produced without using highly toxic and highly corrosive auxiliary raw material and without industrially disadvantageous cumbersome step.

MODE FOR CARRYING OUT THE INVENTION

Figure 1:
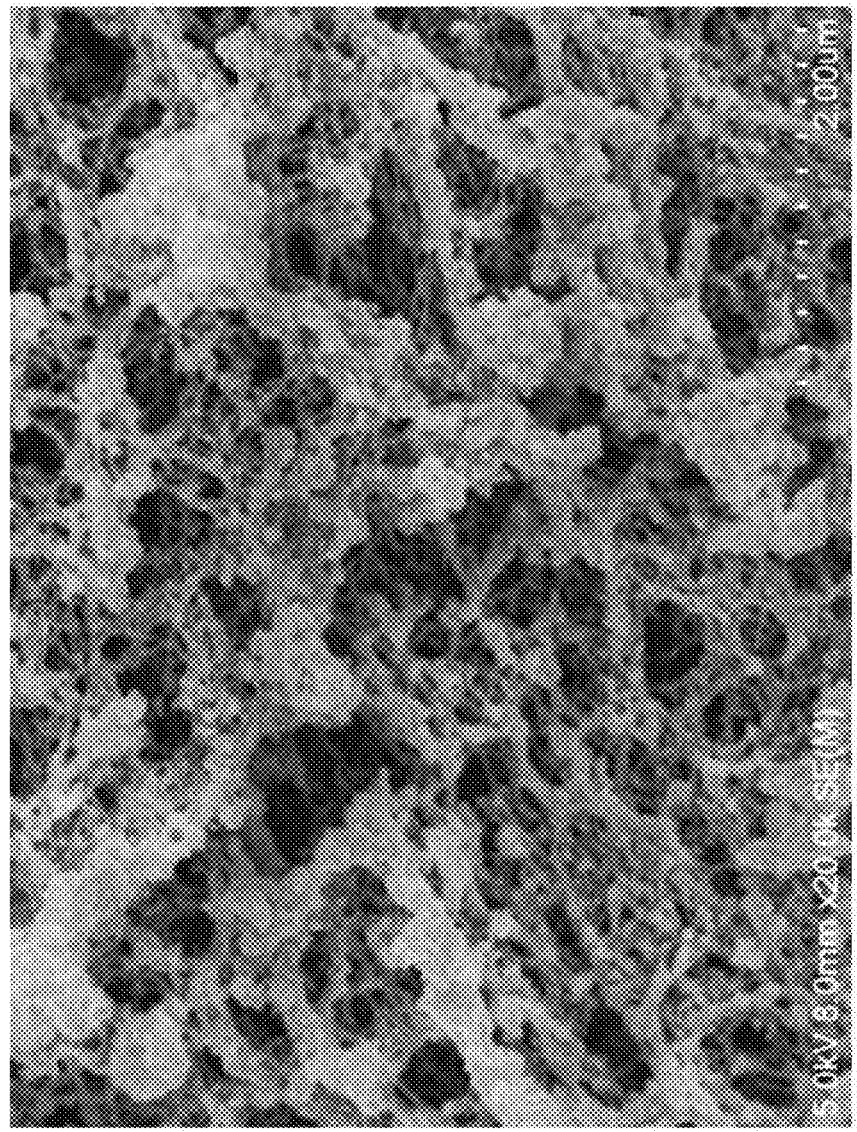
FIG. 1 is a SEM observation image of the magnified surface of the cellulose beads obtained in Example 1 according to the present invention.

The method for producing porous cellulose beads according to the present invention is characterized in comprising (a) the step of preparing a fine cellulose dispersion by mixing a low temperature alkaline aqueous solution and cellulose, (b) the step of preparing a mixed liquid by adding a crosslinking agent to the fine cellulose dispersion, (c) the step of preparing an emulsion by dispersing the mixed liquid in a dispersion medium, and (d) the step of contacting the emulsion with a coagulating solvent to obtain the porous cellulose beads. The applicant of the present application has developed the invention to obtain porous cellulose by dispersing cellulose in sodium hydroxide aqueous solution having low temperature and contacting the dispersion with a coagulating solvent as WO 2012/121258 and others.

The present inventors conducted an experiment to improve the mechanical strength of porous cellulose beads by adding a crosslinking agent to a cellulose dispersion during the process for producing porous cellulose carrier using a low temperature alkaline aqueous solution. As a result, the present inventors found that when a crosslinking agent is added to a cellulose dispersion, an adsorbent having not only high mechanical strength but also larger adsorption amount can be surprisingly obtained, though the reason is not known. The present inventors consider the reason is that a pore suitable for adsorption may be formed by preferably dispersing a crosslinking agent in a cellulose dispersion to form a micro region and transferring the crosslinking agent to a coagulating solvent or a washing solvent. The present inventors did not expect such a phenomenon at first. Hereinafter, the present invention method is described step by step.

Step (a): Step of Preparing Fine Cellulose Dispersion

In the present step, a low temperature alkaline aqueous solution and cellulose are mixed to prepare a fine cellulose dispersion.

In the present invention, the term "low temperature" means a temperature lower than an ordinary temperature. The low temperature may be lower than an ordinary temperature, and is preferably not less than −20° C. since a temperature regulation equipment can be simple and a cost for regulating temperature can be low. In addition, when the low temperature is preferably 10° C. or lower, a cellulose dispersion is hardly colored, and the dispersibility and swellability of cellulose are improved. The low temperature is preferably not less than −10° C. and not more than 20° C. When the temperature is −10° C. or higher, an alkaline aqueous solution can be prevented from being freezed. On the one hand, when the temperature is 20° C. or lower, a cellulose dispersion can be efficiently prepared and can be prevented from being colored. The temperature is more preferably not less than −5° C., even more preferably not less than −2° C., and particularly preferably not less than −1° C. The temperature is most preferably not less than 0° C. in terms of the handling performance of water used for a cellulose dispersion and the easiness of temperature regulation. Furthermore, the temperature is more preferably not more than 15° C., even more preferably not more than 9° C., not more than 5° C., not more than 4° C. or not more than 1° C. In addition, the temperature of not more than 9° C. is preferred, since the sphericity of the obtained porous cellulose beads becomes higher.

An alkali to be used is not particularly restricted as long as an aqueous solution thereof exhibits alkalinity. In terms of availability, lithium hydroxide, sodium hydroxide and potassium hydroxide are preferred; and in terms of safety and price of a product, sodium hydroxide is most preferred.

The concentration of the alkali in the above-described alkaline aqueous solution is not particularly restricted, and is preferably not less than 3 wt % and not more than wt %. When the concentration of the alkali is included in the range, the dispersibility and swellability of cellulose to the alkaline aqueous solution is preferably improved. The concentration of alkali is more preferably not less than 5 wt % and not more than 15 wt %, even more preferably not less than 7 wt % and not more than 10 wt %, and most preferably not less than 8 wt % and not more than 10 wt %.

The kind of the above-described cellulose is not particularly restricted. For example, it is not needed to use substituted cellulose such as a cellulose into which a substituent is introduced to improve solubility, and general unsubstituted cellulose can be used as a raw material, since cellulose may not be dissolved in the present invention method. However, a cellulose powder is preferably used as the cellulose in order to efficiently disperse the cellulose in the alkaline aqueous solution.

The molecular weight of a raw material cellulose to be used is not particularly restricted, and the polymerization degree is preferably not more than 1000. When the polymerization degree is 1000 or less, the dispersibility and swellability of cellulose to the alkaline aqueous solution is preferably improved. In addition, when the polymerization degree is 10 or more, the mechanical strength of the obtained porous cellulose beads preferably becomes high. The polymerization degree is more preferably not less than 50 and not more than 500, even more preferably not less than 100 and not more than 400, particularly preferably not less than 200 and not more than 350, and most preferably not less than 250 and not more than 350.

The concentration of cellulose in the fine cellulose dispersion is not particularly restricted and appropriately adjusted, and for example, may be adjusted to not less than about 1 wt % and not more than about wt %. The concentration is more preferably not less than 2 wt %, even more preferably not less than 4 wt %, and more preferably not more than 15 wt %, even more preferably not more than 10 wt %.

As a method for preparing the fine cellulose dispersion, an ordinary method can be employed. For example, a mixture of the alkaline aqueous solution and cellulose may be vigorously stirred with maintaining the temperature to be lowered.

Step (b): Step of Preparing Mixed Liquid Containing Cellulose and Crosslinking Agent In the present step, a crosslinking agent is added to the above-described fine cellulose dispersion to prepare a mixed liquid.

In the present invention, the term "crosslinking agent" means a compound which has two or more reactive groups capable of covalently binding to the hydroxy group on cellulose so as to crosslink cellulose molecules. The crosslinking agent used in the present invention is not particularly restricted, and conventionally-known crosslinking agent can be preferably used. When it is required to prevent the decrease of the mechanical strength of the porous beads or to increase the mechanical strength, the crosslinking agent which has a functional group capable of binding to the substituent group of cellulose is preferably used. For example, the substituent group of unsubstituted cellulose is a hydroxy group. When a crosslinking reaction is carried out after the formation of the porous beads, i.e. agglomeration, the crosslinking agent used at the time may be preferably also used. In addition, it is preferred that the crosslinking agent is an epoxy group-containing compound, since the functional group can be readily inactivated and non-specific adsorption after the inactivation is small when the used crosslinking agent remains.

The epoxy group-containing compound used in the present invention is not particularly restricted, and is exemplified by a halohydrin such as epichlorohydrin, epibromohydrin and dichlorohydrin; bisepoxide, i.e. bisoxirane, which has two functional groups; and polyepoxide, i.e. polyoxirane, which is multifunctional. In addition, it is preferred that one or more the above-described epoxy group-containing compounds are glycidyl ether compounds, since the adsorption amount becomes larger though the reason is not known.

The above-described glycidyl ether compound is not particularly restricted, and is exemplified by 1,4-butanediol diglycidyl ether, cyclohexanedimethanol diglycidyl ether, resorcinol diglycidyl ether, neopentyl glycol diglycidyl ether, 1,6-hexanediol diglycidyl ether, hydrogenated bisphenol A diglycidyl ether, glycerol diglycidyl ether, trimethylolpropane diglycidyl ether, diglycidyl terephthalate, diglycidyl ortho-phthalate, ethylene glycol diglycidyl ether, diethylene glycol diglycidyl ether, propylene glycol diglycidyl ether, glycerol polyglycidyl ether, pentaerythritol polyglycidyl ether, diglycerol polyglycidyl ether, polyglycerol polyglycidyl ether and sorbitol polyglycidyl ether. To stretch a point, in terms of availability, sorbitol polyglycidyl ether such as Denacol EX-611, EX-612, EX-614, EX-614B and EX-622 manufactured by Nagase ChemteX Corporation; polyglycerol polyglycidyl ether such as Denacol EX-512 and EX-521 manufactured by Nagase ChemteX Corporation; diglycerol polyglycidyl ether such as Denacol EX-421 manufactured by Nagase ChemteX Corporation; glycerol polyglycidyl ether such as Denacol EX-313 and EX-314 manufactured by Nagase ChemteX Corporation; polypropylene glycol diglycidyl ether such as Denacol EX-920 manufactured by Nagase ChemteX Corporation are preferably used.

The solubility of the crosslinking agent used in the present invention in water is preferably not less than 50%. In the present invention, the terms "solubility in water" means the rate of the crosslinking agent which is actually dissolved in water when 10 parts of the crosslinking agent is tried to be dissolved in 90 parts of water at room temperature. When the solubility of the crosslinking agent in water is 50% or more, the compatibility between the crosslinking agent and the cellulose dispersion of the present invention is improved and the sphericity of the beads may be readily maintained. In addition, when the crosslinking agent having a solubility in water of not less than 50% is used, the pore volume and pore size of the obtained beads can be preferably large. Furthermore, the solubility of the crosslinking agent in water is preferably not less than 60% and not more than 100%. The crosslinking agent having a solubility in water of not less than 50% is not particularly restricted, and is exemplified by glycerol polyglycidyl ether Denacol such as EX-313 and EX-314 manufactured by Nagase ChemteX Corporation; diglycerol polyglycidyl ether such as Denacol EX-421 manufactured by Nagase ChemteX Corporation; polyglycerol polyglycidyl ether such as Denacol EX-512 and EX-521 manufactured by Nagase ChemteX Corporation; sorbitol polyglycidyl ether such as Denacol EX-614 and EX-614B manufactured by Nagase ChemteX Corporation; ethylene glycol diglycidyl ether such as Denacol EX-810 and EX-811 manufactured by Nagase ChemteX Corporation; diethylene glycol diglycidyl ether such as Denacol EX-850 and EX-851 manufactured by Nagase ChemteX Corporation; polyethylene glycol diglycidyl ether such as Denacol EX-821, EX-830, EX-832, EX-841, EX-861, EX-911, EX-941, EX-920 and EX-931 manufactured by Nagase ChemteX Corporation.

The viscosity of the crosslinking agent used in the present invention is preferably not less than 100 mPa·s and not more than 50000 mPa·s. When the viscosity of the crosslinking agent is included in the range, the adsorption amount may become larger though the reason is not known. The present inventor consider the reason is that the pore which is advantageous to adsorption may be readily formed in the beads, though the details are unclear. In addition, when the crosslinking agent having a viscosity of 100 mPa·s or more is used, particle diameter of the obtained beads may not be excessively large, though the reason is unknown. The viscosity is more preferably not less than 100 mPa·s and not more than 30000 mPa·s, even more preferably not less than 150 mPa·s and not more than 25000 mPa·s, and particularly preferably not less than 150 mPa·s and not more than 5500 mPa·s. The viscosity can be measured by using a Hoeppler viscometer. The crosslinking agent having a viscosity of not less than 100 mPa·s and not more than 50000 mPa·s is not particularly restricted, and is exemplified by resorcinol diglycidyl ether such as Denacol EX-201 manufactured by Nagase ChemteX Corporation; neopentyl glycol diglycidyl ether such as Denacol EX-211 manufactured by Nagase ChemteX Corporation; 1,6-hexanediol diglycidyl ether such as Denacol EX-212 manufactured by Nagase ChemteX Corporation; hydrogenated bisphenol A diglycidyl ether such as Denacol EX-252 manufactured by Nagase ChemteX Corporation; glycerol polyglycidyl ether such as Denacol EX-313 and EX-314 manufactured by Nagase ChemteX Corporation; trimethylolpropane polyglycidyl ether such as Denacol EX-321 manufactured by Nagase ChemteX Corporation; pentaerythritol polyglycidyl ether such as Denacol EX-411 manufactured by Nagase ChemteX Corporation; diglycerol polyglycidyl ether such as Denacol EX-421 manufactured by Nagase ChemteX Corporation; polyglycerol polyglycidyl ether such as Denacol EX-512 and EX-521 manufactured by Nagase ChemteX Corporation; sorbitol polyglycidyl ether such as Denacol EX-611, EX-612, EX-614, EX-614B and EX-622 manufactured by Nagase ChemteX Corporation; diglycidyl terephthalate such as Denacol EX-711 manufactured by Nagase ChemteX Corporation; diglycidyl ortho-phthalate such as Denacol EX-721 manufactured by Nagase ChemteX Corporation; diethylene glycol diglycidyl ether such as Denacol EX-850 and EX-851 manufactured by Nagase ChemteX Corporation; polyethylene glycol diglycidyl ether such as Denacol EX-821, EX-830, EX-832, EX-841, EX-861 and EX-931 manufactured by Nagase ChemteX Corporation.

An amount of the crosslinking agent to be used in the present step may be appropriately adjusted and is not particularly restricted, and for example, may be adjusted to not less than 0.5 times by mass and not more than 10 times by mass to the cellulose which is contained in the above-described cellulose dispersion. The amount of the crosslinking agent in the mixed liquid of the fine cellulose dispersion and the crosslinking agent is preferably not less than 1 mass % and not more than mass %. The ratio is more preferably not less than 2 mass % and more preferably not more than 15 mass %.

A method for adding the above-described crosslinking agent to the cellulose dispersion is not particularly restricted. For example, the crosslinking agent may be added to the prepared cellulose dispersion, or the crosslinking agent may be added during the preparation of the cellulose dispersion. In addition, whether the crosslinking agent is in the form of a liquid or solid, the crosslinking agent may be added as it is, a solution in which the crosslinking agent is dissolved in a solvent may be added, or a dispersion or slurry of the crosslinking agent may be added. The solvent and dispersion medium in such cases are not particularly restricted, and an organic solvent or water may be used. The temperature when the crosslinking agent is added is not particularly restricted, and is preferably not more than 25° C. in order to prevent the beads from being colored. In addition, when the temperature is not less than 0° C., the crosslinking agent may sufficiently exhibit the effect.

It is not necessarily needed that the crosslinking agent is homogeneously dispersed or dissolved in the cellulose dispersion. When it is needed to homogeneously disperse or dissolve the crosslinking agent, a procedure such as natural diffusion, stirring and shaking may be carried out.

As a method for preparing porous beads from the above-described mixed liquid, a publically-known agglomeration method described in WO 2012/121258 and others may be employed. In addition, a publically-known crosslinking method may be further applied to the porous beads of the present invention. The contents of WO 2012/121258 are incorporated herein by reference. Hereinafter, subsequent steps are briefly described.

Step (c): Step of Preparing Emulsion

In the present step, an emulsion is prepared by dispersing the above-described mixed liquid in a dispersion medium.

As the dispersion medium which constitutes of the emulsion, an animal and plant fat and oil, a hydrogenated animal and plant fat and oil, a fatty acid glyceride, an aliphatic hydrocarbon solvent and an aromatic hydrocarbon solvent are exemplified. In addition, a surfactant such as a non-ionic surfactant may be used.

An animal and plant fat and oil is exemplified by palm oil, shea butter, sal fat, illipe butter, lard, beef fat, canola oil, rice oil, peanut oil, olive oil, corn oil, soybean oil, perilla oil, cotton oil, sunflower oil, evening primrose oil, sesame oil, safflower oil, coconut oil, cacao oil, palm kernel oil, fish oil, wakame seaweed oil, kelp oil and the like. A hydrogenated animal and plant fat and oil is exemplified by palm hardened oil, palm extremely hardened oil, canola hardened oil, canola extremely hardened oil, soybean hardened oil, hardened oil of lard, hardened fish oil and the like. A fatty acid triglyceride may be any one of tri-, di- and mono-glyceride, and is exemplified by stearyl glyceride, palmitin glyceride, lauryl glyceride and the like. An aliphatic hydrocarbon solvent is exemplified by beeswax, candelilla wax, rice bran wax and the like. An aromatic hydrocarbon solvent is exemplified by benzene, toluene, chlorobenzene, dichlorobenzene and the like.

In order to prepare the emulsion, an appropriate amount of a surfactant may be added. Such a surfactant is exemplified by a sorbitan fatty acid ester such as sorbitan laurate, sorbitan stearate, sorbitan oleate, sorbitan trioleate and the like.

An amount of the dispersion medium to be used may be adjusted so that droplets of the above-described mixed liquid can be sufficiently dispersed. For example, the amount may be adjusted to one or more times by mass to the above-described mixed liquid. On the one hand, when the amount of the dispersion medium is excessively large, an amount of a waste liquid is excessively increased; therefore, the ratio is preferably not more than 10 times by mass. The ratio is more preferably not less than 2 times by mass, even more preferably not less than 4 times by mass, and not more than 8 times by mass, even more preferably not more than 7 times by mass.

The emulsion may be prepared by an ordinary method. For example, the emulsion can be prepared by vigorously stirring a mixture of the above-described mixed liquid, the dispersion medium and the surfactant.

Step (d): Step of Coagulation

Next, the porous cellulose beads are obtained by bringing the above-described emulsion into contact with a coagulating solvent in order to extract the solvent from droplets of the fine cellulose dispersion.

The coagulating solvent is not particularly restricted as long as the coagulating solvent has an affinity for the solvent of the fine cellulose dispersion, and is exemplified by an alcohol solvent and a mixed solvent of water and an alcohol solvent. Such an alcohol solvent is exemplified by $C_{1-4}$ alcohol such as methanol, ethanol, n-propanol, isopropanol, n-butanol, isobutanol, s-butanol and t-butanol. For example, a ratio of water and alcohol in an alcohol aqueous solution may be adjusted to water: alcohol solvent=80:20 to 5:95 by volume.

An amount of the coagulating solvent to be used is not particularly restricted and appropriately adjusted, and for example, may be adjusted to not less than about 20 v/w % and not more than about 150 v/w % to the above-described mixed liquid to be used.

A method for coagulation is not particularly restricted, and it is preferred that the coagulating solvent is added to the vigorously stirred emulsion so that droplets are not bound each other, since the emulsion is sometimes unstable.

After the coagulating solvent is added, the coagulated porous cellulose beads are isolated by filtration, centrifuge or the like, and may be washed with water, an alcohol or the like. The obtained porous cellulose beads may be classified using a sieve or the like in order to control the particle size to be uniform.

Step (e): Step of Crosslinking Porous Cellulose Beads

It is preferred that the thus obtained porous cellulose beads are crosslinked to obtain crosslinked porous cellulose beads using a crosslinking agent in order to improve the strength in addition to that the crosslinking agent is added in the above-described Step (b) of preparing mixed liquid containing cellulose and a crosslinking agent.

In the present step, the crosslinking condition and crosslinking agent are also not particularly restricted. For example, the method described in WO 2008/146906 can be employed.

The additional crosslinking agent is exemplified by a halohydrin such as epichlorohydrin, epibromohydrin and dichlorohydrin; bisepoxide, i.e. bisoxirane, which has two functional groups; and polyepoxide, i.e. polyoxirane, which is multifunctional. Only one crosslinking agent may be used alone, or two or more crosslinking agents may be used in combination.

A solvent used in the reaction for crosslinking porous cellulose beads by the additional crosslinking agent may be appropriately selected, and is exemplified by a water-miscible organic solvent in addition to water. The example of such a water-miscible organic solvent includes an alcohol solvent such as methanol, ethanol and isopropanol, and a nitrile solvent such as acetonitrile. Two or more solvents may be mixed to be used for the crosslinking reaction.

The crosslinking reaction may be carried out multiple times, and the reaction solvent and the additional crosslinking agent may be changed in each time. For example, a first crosslinking reaction may be carried out in a water-miscible organic solvent, and a final crosslinking reaction may be carried out in water. In such a case, the solvent compositions from second to second last reactions may be the same as or different from that of a first reaction or a last reaction, or an intermediate composition between those of a first reaction and a last reaction. Alternatively, all of the reactions may be carried out in water. The conditions are also applied to the additional crosslinking agent. When the crosslinking reaction is carried out multiple times, it is preferred that the crosslinked porous cellulose is washed with water or the like to remove the additional crosslinking agent between the crosslinking reactions.

A base may be added to the reaction mixture in order to accelerate the crosslinking reaction. Such a base is exemplified by an alkali metal hydroxide such as sodium hydroxide and potassium hydroxide; an alkali metal hydrogencarbonate salt such as sodium hydrogencarbonate and potassium hydrogencarbonate; an alkali metal carbonate salt such as sodium carbonate and potassium carbonate; an organic base such as triethylamine and pyridine.

After the crosslinking reaction, the crosslinked porous cellulose beads may be washed with water or the like, since the beads is insoluble.

Step (f): Step of Immobilizing Ligand

An adsorbent can be obtained by immobilizing a ligand which interacts with a target substance on the porous cellulose beads according to the present invention. The adsorbent obtained by the present invention is less likely to exhibit non-specifical adsorption; therefore, a pharmaceutical and a treatment with high safety can be provided and further, labor for an intermediate washing step can be saved as much as possible during purification and treatment by using the adsorbent.

In the present invention, the term "ligand" means an affinity ligand which has a specific affinity for a target substance to be purified by being adsorbed on the adsorbent and which interacts with the target substance. For example, when a target substance is an antibody, a ligand is exemplified by an antigen, a protein, a peptide fragment and the like which specifically interact with the antibody. The ligand used for the adsorbent according to the present invention is not particularly restricted as long as the ligand has a specific affinity for a target substance which should be purified using the adsorbent according to the present invention.

A method for immobilizing a ligand on the porous cellulose beads according to the present invention is not particularly restricted, and an ordinary method may be employed. For example, various immobilization methods are exemplified, such as a method for immobilizing an amino group-containing ligand using a cyanogen bromide method, a trichlorotriazine method, an epoxy method, a tresyl chloride method, a periodic acid oxidation method, a divinylsulfonic acid method, a benzoquinone method, a carbonyldiimidazole method, an acyl azide method or the like; a method for immobilizing a hydroxy group-containing ligand using an epoxy method, a diazo coupling method or the like; a method for immobilizing a thiol group-containing ligand using an epoxy method, a tresyl chloride method, a divinylsulfonic acid method or the like; a method for immobilizing a carboxy acid group-containing ligand and a formyl group-containing ligand on an aminated carrier, as described in Kenichi KASAI et al., "Affinity chromatography" published by Tokyo Kagakudoujin, 1991, Table 8-1, Table 8-2 and FIG. 8-15. The contents of the document are incorporated by reference herein.

The adsorbent according to the present invention can be used as an adsorbent for purification, particularly as an adsorbent for purifying an antibody pharmaceutical and medical adsorbent, which have attracted attention in recent years. An ligand used for an adsorbent for purifying an antibody pharmaceutical is not particularly restricted, and is exemplified by an amino group-containing ligand such as an antigen and a protein which have highly specific affinity for an antibody; Protein A, Protein G, Protein L, and variants thereof; and a peptide having an antibody binding activity.

In particular, an adsorbent which is prepared by immobilizing Protein A, Protein G or a variant thereof as a ligand on a porous carrier has attracted attention as an adsorbent capable specifically adsorbing an immunoglobulin, i.e. IgG. The above-described Protein A used in the present invention is not particularly restricted, and natural Protein A, transgenic Protein A and the like may be used without restriction. In addition, a substance containing an antibody-binding domain, a variant thereof or an oligomer thereof, a fused protein and the like may be used. The polymerization number of such an oligomer may be not less than 2 and not more than 10. In addition, Protein A and the like to be used can be produced from an extract obtained from fungus body or a culturing supernatant by combining and/or repeating a purification method selected from a molecular weight fractionation, a fractional precipitation and the like in which various chromatography and membrane separation technique are utilized. Such a chromatography is exemplified by ion-exchange chromatography, hydrophobic interaction chromatography, gel filtration chromatography and hydroxyapatite chromatography. In particular, it is preferred that Protein A is obtained by the method described in WO 2006/004067, U.S. Pat. No. 5,151,350, WO 2003/080655, JP 2006-304633 A, WO 2010/110288 or WO 2012/133349. The contents described in the publications are incorporated by reference. The absorbent according to the present invention on which Protein A is immobilized can be also utilized as an adsorbent used for treating dilated cardiomyopathy and the like. In addition, the absorbent according to the present invention on which dextran sulfate or the like is immobilized can be utilized as an adsorbent used for treating hypercholesterolemia.

A method for introducing a ligand on the porous cellulose beads may be selected from the above-described various immobilization methods, and it is more preferred that a reaction between a formyl group that a porous particle has and an amino group of a ligand is utilized to carry out immobilization. For example, the method described in WO 2010/064437 is used. All of the contents of the publication are incorporated by reference herein.

An amount of the ligand to be immobilized on the adsorbent according to the present invention is not particularly restricted, and for example, may be adjusted to not less than 1 mg and not more than 1000 mg per 1 mL of the porous cellulose beads. When the ratio is 1 mg or more, an adsorption amount of a target substance preferably becomes large. When the ratio is 1000 mg or less, the production cost may be preferably reduced. An amount of the ligand to be immobilized per 1 mL of the porous cellulose beads is more preferably not less than 2 mg, even more preferably not less than 4 mg, particularly preferably not less than 5 mg, and more preferably not more than 500 mg, even more preferably not more than 250 mg, particularly preferably not more than 200 mg, most preferably not more than 100 mg.

The use application of the adsorbent according to the present invention is not particularly restricted, and the adsorbent is preferably used as a medical adsorbent. In particular, the adsorbent is preferably used as a therapeutic adsorbent for adsorbing a large-sized disease substance such as LDL cholesterol to be removed, since the surface porosity of the adsorbent is improved. In addition, the adsorbent can be used as various chromatographic carriers, particularly as an industrial chromatographic carrier which is used for filling a large-diameter column. In particular, when the adsorbent is used as an adsorbent for purifying an antibody pharmaceutical, of which demand has been very heavy recently, the effect of the adsorbent can be exhibited. In terms of the above points, the porous cellulose beads according to the present invention are preferably used for producing an adsorbent on which Protein A, Protein G or Protein L is immobilized.

A target substance can be purified by using the adsorbent according to the present invention. Specifically, the adsorbent of the present invention may be contacted with a solution of a target substance. A contacting method is not restricted, and the adsorbent according to the present invention may be added to a solution which contains a target substance, or a target substance may be selectively adsorbed on the adsorbent according to the present invention by filling a column with the present invention adsorbent as described above and flowing a solution containing the target substance through the column. In particular, when a column is filled with the present invention adsorbent, a solution can be flowed at high speed so that a target substance can be efficiently purified, since the strength of the present invention adsorbent is high.

Next, the present invention adsorbent on which a target substance is selectively adsorbed is separated from a solution by filtration, centrifugation or the like. By such a step, a target substance can be separated from other substances. In addition, a target substances is separated from the present invention adsorbent by using an eluate. As such an eluate, for example, an acidic buffer solution of which pH value is not less than about 2.5 and not more than about 4.5 may be used.

The present application claims the benefit of the priority date of Japanese patent application No. 2013-215121 filed on Oct. 15, 2013. All of the contents of the Japanese patent application No. 2013-215121 filed on Oct. 15, 2013, are incorporated by reference herein.

EXAMPLES

Hereinafter, the example of the present invention is described. However, the present invention is not restricted to the following examples in any way. First, methods for evaluating the physical properties of the produced porous cellulose beads are described.

Test Example 1: SEM Observation of Beads Surface

The beads obtained in each Production example and Example were washed with five times amount by volume of 30% ethanol to replace the liquid part contained in the beads by 30% ethanol. Then, the beads were similarly treated with 50% ethanol, 70% ethanol, 90% ethanol, special grade ethanol, special grade ethanol and special grade ethanol in turns in order to replace the liquid part by ethanol. Further, the beads were similarly treated by a mixed solvent of t-butyl alcohol/ethanol=3/7. Next, the beads were treated with mixed solvents of t-butyl alcohol/ethanol=5/5, 7/7, 9/1, 10/0, 10/0 and 10/0 in turns in order to replace the liquid part by t-butyl alcohol, and then freeze-dried. The freeze-dried beads were subjected to deposition treatment using gold/palladium as a deposition source, and SEM image was photographed.

Test Example 2: Measurement of Dynamic Binding Capacity at RT (Residence Time) of 3 Minutes (1) Preparation of Solution
The following solutions were prepared.
Liquid A: phosphate buffer with a pH of 7.4 (manufactured by SIGMA)
Liquid B: 35 mM sodium acetate with a pH of 3.5, prepared from acetic acid (manufactured by NACALAI TESQUE, INC.), sodium acetate and RO water
Liquid C: 1 M acetic acid prepared from acetic acid (manufactured by NACALAI TESQUE, INC.) and RO water
Liquid D: 1 mg/mL human polyclonal IgG solution, prepared from 1500 mg/10 mL of "Gamma-globulin NICHI-YAKU" (manufactured by NIHON PHARMACEUTICAL CO., LTD.) and Liquid A
Liquid E: 6 M urea prepared from urea (manufactured by KANTO CHEMICAL CO., INC.) and RO water
Each solution was deaerated before use.

(2) Filling and Preparation
As a column chromatography apparatus, AKTAexplorer 100 (manufactured by GE Healthcare Corporation) was used. A 22 μm mesh was attached to a column having a diameter of 0.5 cm and height of 15 cm, and 3 mL of the adsorbent according to the present invention was added into the column. The column was filled with the adsorbent by flowing 20% ethanol aqueous solution prepared from ethanol (manufactured by Wako Pure Chemical Industries, Ltd.) and RO water at a linear speed of 450 cm/h for 1 hour. On a fraction collector, 15 mL correcting tubes were set. Into the correcting tubes for an eluent, a neutralizing liquid was preliminarily added.

(3) Purification of IgG
Through the above-described column, 9 mL of Liquid A was flowed at a linear speed of 300 cm/h and then Liquid D was flowed at a linear speed of 300 cm/h till 10% of IgG passed with monitoring UV. A loading amount of IgG when 5% of IgG passed through was determined to be 5% DBC at RT of 3 minutes. Next, after 30 mL of Liquid A was flowed at a linear speed of 300 cm/h, 30 mL of Liquid B was flowed at a linear speed of 300 cm/h to elute IgG. Then, 9 mL of Liquid C was flowed at a linear speed of 300 cm/h and 9 mL of Liquid E was flowed at a linear speed of 300 cm/h for recycling.

Test Example 3: Measurement of Dynamic Binding Capacity (1) Preparation of Solution
The following Liquids A to E and Neutralizing liquid were prepared and deaerated before use.
Liquid A: PBS buffer with a pH of 7.4, prepared from "Phosphate buffered saline" (manufactured by SIGMA) and water purified using an osmosis membrane, i.e. RO water
Liquid B: 35 mM sodium acetate aqueous solution with a pH of 3.5, prepared from acetic acid, sodium acetate and RO water
Liquid C: 1 M acetic acid aqueous solution prepared from acetic acid and RO water
Liquid D: IgG aqueous solution having a concentration of 3 mg/mL, prepared from polyclonal antibody ("Gammagard" manufactured by Baxter) and the above-described Liquid A
Liquid E: 6 M urea aqueous solution prepared from urea and RO water
Neutralizing liquid: 2 M tris(hydroxymethyl)aminomethane prepared from tris(hydroxymethyl)aminomethane and RO water (2) Filling and Preparation
As a column chromatography apparatus, AKTAexplorer100 (manufactured by GE Healthcare Corporation) was used. Into a column having a diameter of 0.5 cm and height of 15 cm, 3 mL of the adsorbent sample was added. The column was filled with the adsorbent sample by flowing 0.2 M NaCl aqueous solution prepared from RO water at a linear speed of 230 cm/h for 15 minutes. On a fraction collector, 15 mL correcting tubes were set. Into the correcting tubes for an eluent, Neutralizing liquid was preliminarily added.

(3) Purification of IgG
Through the above-described column, 15 mL of Liquid A was flowed and then necessary amount of Liquid D was flowed. Next, after 21 mL of Liquid A was flowed, 12 mL of Liquid B was flowed to elute IgG. Then, 6 mL of Liquid C, 6 mL of Liquid E and 15 mL of Liquid A were flowed. The flow speed of each liquid was adjusted to 0.5 mL/min or 1 mL/min so that the time of contact between the adsorbent and each liquid was 6 minutes or 3 minutes.

(4) Dynamic Binding Capacity
A dynamic binding capacity of IgG was calculated from the volume of the adsorbent and the amount of IgG which was adsorbed on the adsorbent by 5% of IgG passed through. The dynamic binding capacity is referred to as "5% DBC".

Test Example 4: 20% Compression Stress (1) Preparation of Sample

Pure water was added to the sample beads to prepare a slurry of which concentration was about 50 vol %. The slurry was homogenized by stirring and then deaerated under reduced pressure for 30 minutes or more. The homogenization and deaeration procedure was repeated 3 times to obtain a deaerated slurry. Separately, the processed object was changed to pure water and the above homogenization and deaeration procedure was carried out for 90 minutes or more to obtain deaerated water.

(2) Preparation of Beads-Filled Syringe

A disposable filter (pore diameter: 5.00 µm, hydrophilic) was attached to the tip of 2.5 mL disposable syringe with a lure lock (Product name: NORM-JECT, manufactured by HANKE SASS WOLF). The piston was removed from the syringe, about 2 mL of deaerated water was added from the rear end side of the syringe, and the deaerated slurry was added before the added deaerated water fell below the gauge line of 0 mL. An aspirator was connected to the secondary side of the disposable filter to carefully aspirate the above-described deaerated slurry while the liquid surface did not fall below the top surface of the beads. The suction was stopped when the liquid level was decreased to about 0.5 mL in addition to the volume of the precipitated beads. The subsequent procedures were carried out with adding the above-described deaerated water so that the liquid level did not fall below the top surface of the beads. The height of the beads was adjusted to the gauge line of 1.5 mL by adding the above-described deaerated slurry or removing the beads with giving vibration until it was confirmed that the top surface of the beads was not dropped any more even when vibration was given. Deaerated water was added slowly so that the beads were not flied up until deaerated water overflowed, and then the piston was inserted carefully so as not to mix air bubbles. Hereinafter, the obtained syringe is referred to as "beads-filled syringe".

(3) Measurement

A 10 K load cell was installed on "FUDOH RHEO METER" (manufactured by RHEOTECH), the dial of displacement speed was set at 2 cm/MIN, and the above-described beads-filled syringe was placed. Then, the displacement of the piston was started. The relationship between the displacement and the stress was recorded, and 20% compression stress was calculated in accordance with the following formula.

20% Compression stress=(Stress when filling beads was pressed by 20%)−(Stress just before piston reaches beads surface)

Test Example 5: Measurement of $K_{av}$: Gel Distribution Coefficient

In distilled water, 22.8 mL of the porous cellulose beads were dispersed. The mixture was deaerated for 30 minutes. A column ("Tricorn 10/300" manufactured by GE healthcare Japan) was filled with the deaerated porous cellulose beads. The measurement was carried out using a size exclusion chromatography system (manufactured by SHIMADZU CORPORATION). The system contained DGU-20A3, RID-10A, LC-20AD, SIL-20AC and CTO-20AC, and "LCSolution" was used as a software.

The following dextran or glucose to be used as a marker was dissolved in 50 mM phosphate buffer (pH 7.5) containing 1M NaCl.

TABLE 1

| Molecular weight | Viscosity radius [nm] | Concentration [mg/mL] | Amount of injected marker [µL] |
|---|---|---|---|
| 1185000 | 27.0 | 3 | 40 |
| 667800 | 16.7 | 3 | 40 |
| 80900 | 6.8 | 1 | 80 |
| 48600 | 5.5 | 1 | 80 |
| 23800 | 3.9 | 1 | 80 |
| 11600 | 2.6 | 1 | 80 |
| 5220 | 1.8 | 1 | 80 |
| 180 | 0.4 | 10 | 40 |

While 50 mM phosphate buffer (pH 7.5) containing 1M NaCl was flowed through the column at a flow speed of 0.6 mL/min, a solution of dextran having a molecular weight of $4 \times 10^7$ was firstly injected and the amount of liquid to be flowed through the column from the injection to the observation of the peak was measured by RI monitor in order to determine the volume except for the beads part in the column. The concentration of dextran having a molecular weight of $4 \times 10^7$ in the solution was adjusted to 10 mg/mL, and the injection amount was set to 40 µL. Then, the amount of each marker solution to be flowed through the column was similarly measured. The measured values were plugged in the following formula to calculate the value of $K_{av}$.

$K_{av}=(V_R-V_0)/(V_t-V_0)$ wherein $V_R$ is the amount (mL) of a liquid to be flowed through the column from the injection of each marker solution to the observation of the peak, $V_0$ is the amount (mL) of a liquid to be flowed through the column from the injection of the solution of dextran having a molecular weight of $4 \times 10^7$ to the observation of the peak, $V_t$ is the volume (mL) of the beads in the column.

Test Example 6: Calculation of Pore Size Distribution

The viscosity radius of each marker and the value of $K_{av}$ obtained as the above were plugged in the following formula in order to calculate the radius of the porous cellulose beads pore into which each marker was incorporated.

$K_{av}=(1-r_m/r_p)^2$ wherein $r_m$ is the each marker radius (nm) calculated from viscosity, $r_p$ is the radius (nm) of the pore into which each marker was incorporated.

The calculated pore radius of porous cellulose beads was plotted on an abscissa axis, and the pore size distribution when the volume $(V_R-V_0)$ of the pore into which the marker having a molecular weight of 180 was incorporated was assumed to be 100% was plotted on a longitudinal axis.

Test Example 7: Calculation of Pore Size Distribution

The pore diameter when the cumulative pore volume was 50% was determined on the basis of the graph prepared in Test example 6.

Production Example 1: Preparation of Non-Orientation-Controlled Protein A

The non-orientation-controlled Protein A used in the present invention had an amino acid sequence of SEQ ID NO. 1. The Protein A corresponds to a part of the Protein A derived from *Staphylococcus aureus* other than S domain, i.e. signal sequence, and X domain, i.e. cell wall binding domain, and is described as SPA' in WO 2006/004067. The Protein A was prepared in accordance with Examples described in WO 2006/004067. The contents of WO 2006/004067 are incorporated by reference herein.

Production Example 2: Preparation of Orientation-Controlled Alkali-Resistant Protein A The pentamer of modified C domain described in WO 2012/133349 was prepared as orientation-controlled alkali-resistant Protein A with reference to WO 2012/133349. The orientation-controlled alkali-resistant Protein A had an amino acid sequence of SEQ ID NO. 2. The contents of WO 2012/133349 are incorporated by reference herein.

Example 1

(1) Preparation of Alkaline Aqueous Solution
Using sodium hydroxide (manufactured by Wako Pure Chemical Industries, Ltd.) and distilled water, 28.4 wt % sodium hydroxide aqueous solution was prepared. The temperature thereof was adjusted to 4° C.

(2) Preparation of Cellulose Dispersion Containing Crosslinking Agent
Into a separable flask, 79 g of distilled water and 5.9 g of cellulose were added. The mixture was stirred using rushton turbine blades at 150 to 200 rpm for 30 minutes until the temperature of the slurry became 4° C. Then, 36 g of 28 wt % sodium hydroxide aqueous solution which was cooled to 4° C. was added thereto. The mixture was maintained with stirring at 500 rpm for 30 minutes. Next, 12 g of glycerol polyglycidyl ether ("Denacol EX-314" manufactured by Nagase ChemteX Corporation) was added as a crosslinking agent to the prepared cellulose dispersion. The mixture was stirred at 500 rpm for 15 minutes.

(3) Preparation of Porous Cellulose Beads by Liquid-Liquid Dispersion
To the above-described cellulose dispersion, 833 g of 1 wt % sorbitan monooleate solution in o-dichlorobenzene was added. The mixture was stirred at 4° C. and 600 rpm for 15 minutes to disperse cellulose droplets, and 74 mL of methanol as a coagulating solvent was added thereto. The mixture was stirred at 4° C. and 600 rpm for 30 minutes. Then, the solution was removed by filtration using a glass filter ("26G-3" manufactured by TOP), and the porous cellulose beads were washed to be obtained using 5 times volume of methanol and 5 times volume of distilled water in turns.

(4) Classification of Porous Cellulose Beads
The obtained porous cellulose beads were subjected to wet classification using sieves of 38 μm and 90 μm.

(5) Crosslinking of Porous Cellulose Beads
To 20 mL of the above-described classified porous cellulose beads, distilled water was added so that the volume was adjusted to 30 mL. The mixture was transferred into a reaction vessel. Into the reaction vessel, 2.3 g of glycerol polyglycidyl ether ("Denacol EX-314" manufactured by Nagase ChemteX Corporation) was added as a crosslinking agent. The mixture was heated to 40° C. with stirring. After the temperature was adjusted to 40° C., the mixture was stirred for 30 minutes. Then, 7.1 mL of 2 N NaOH aqueous solution was prepared from sodium hydroxide (manufactured by NACALAI TESQUE, INC.) and distilled water, and each ¼ of the solution was added per 1 hour. During the addition, the temperature was maintained at 40° C. with stirring. After the last ¼ amount of the solution was added, the mixture was stirred at the same temperature for 1 hour. After the reaction, the beads were washed with times or more volume of distilled water with suction-filtration to obtain first crosslinked beads. The obtained first crosslinked beads were subjected to the same crosslinking reaction once more to obtain second crosslinked beads.

The obtained second crosslinked beads were transferred into a vessel, and distilled water was added thereto so that the total amount was adjusted to 10 times volume of the crosslinked porous cellulose beads. The mixture was heated using an autoclave at 120° C. for 60 minutes. After the mixture was cooled to room temperature, the beads were washed with 5 times or more volume of distilled water as much as the beads to obtain the autoclaved second crosslinked beads. The SEM observation image of the beads surface is shown as FIG. 1.

(6) Preparation of Adsorbent
An adsorbent on which Protein A was immobilized was prepared in accordance with the following procedures. To 11.0 mL of the crosslinked porous cellulose beads obtained in the above-described (5), RO water was added to adjust the total amount to 17.0 mL. The mixture was added into 50 mL centrifuge tube. The centrifuge tube was set on a mix rotor ("MIX ROTOR MR-3" manufactured by AS ONE Corporation) to stir the mixture. Then, 6.0 mL of 8.64 mg/mL sodium periodate aqueous solution prepared by dissolving sodium periodate in RO water was added thereto. The mixture was stirred at 25° C. for 1 hour. After the reaction, the beads were washed with RO water on a glass filter ("11GP100" manufactured by SIBATA SCIENTIFIC TECHNOLOGY LTD.) till the electrical conductivity of the filtrate became 1 μS/cm or lower to obtain formyl group-containing crosslinked porous cellulose beads. The electrical conductivity of the filtrate obtained by washing was measured using a conductivity meter ("ECTester10 Pure+" manufactured by EUTECH INSTRUMENTS). On a glass filter ("11GP100" manufactured by SIBATA SCIENTIFIC TECHNOLOGY LTD.), 9.0 mL of the obtained formyl group-containing crosslinked porous cellulose beads were put, and 30 mL of buffer containing 0.5 M trisodium citrate dihydrate (manufactured by KANTO CHEMICAL CO., INC.) and 0.15 M sodium chloride (manufactured by KANTO CHEMICAL CO., INC.) was flowed to replace the liquid within the beads by the trisodium citrate aqueous solution. After the replacement, the formyl group-containing crosslinked porous cellulose beads were added into a centrifuge tube using the above-described buffer. After the formyl group-containing crosslinked porous cellulose beads were precipitated, the total volume was adjusted to 14.0 mL by removing the supernatant.

Into the centrifuge tube, 5.327 g of 67.58 mg/mL solution of the Protein A produced in the above-described Production example 1 was added. Then, the pH value was adjusted to 12 using 0.08 N sodium hydroxide prepared from sodium hydroxide (manufactured by NACALAI TESQUE, INC.) and RO water at 6° C., and the reaction was carried out at 6° C. for 23 hours with stirring by a mixing rotor ("MIX ROTOR MR-3" manufactured by AS ONE Corporation). After the reaction for 23 hours, the pH of the reaction mixture was adjusted to 5.0 using 2.4 M citric acid prepared from citric acid (manufactured by KANTO CHEMICAL CO., INC.) and RO water. Then, the mixture was stirred at 6° C. for 4 hours using a mixing rotor ("MIX ROTOR MR-3" manufactured by AS ONE Corporation). Next, 0.39 mL of 5.5% dimethylamine borane (DMAB) aqueous solution prepared from dimethylamine borane (manufactured by KISHIDA CHEMICAL Co., Ltd.) and RO water was added thereto, and the mixture was stirred at 6° C. for 1 hour. Then, the reaction temperature was increased to 25° C., and the reaction was carried out at 25° C. for 18 hours with stirring by a mixing rotor ("MIX ROTOR MR-3" manufactured by AS ONE Corporation). After the reaction, the amount of the unreacted Protein A was determined by measuring UV absorbance of absorption maximum at about 278 nm of the reaction mixture, and the amount of the immobilized Protein A was calculated by subtracting the determined amount value from the used ligand amount. The beads after the reaction was washed with RO water of which volume was threefold of the volume of the beads on a glass filter ("11GP100" manufactured by SIBATA SCIENTIFIC TECHNOLOGY LTD.). Then, threefold volume amount of 0.1 M citric acid aqueous solution prepared from citric acid monohydrate (manufactured by KANTO CHEMICAL CO., INC.) and RO water was added and further 0.1 M citric acid monohydrate was added to the beads so that the total volume was adjusted to 30 mL or more. The mixture was added into a centrifuge tube and stirred at 25° C. for 30 minutes to carry out acid washing.

After the acid washing, the beads were washed with RO water of which volume was threefold of the volume of the beads on a glass filter ("11GP100" manufactured by SIBATA SCIENTIFIC TECHNOLOGY LTD.). Next, threefold volume of an aqueous solution of 0.05 M sodium hydroxide and 1 M sodium sulfate prepared from sodium hydroxide (manufactured by NACALAI TESQUE, INC.), sodium sulfate (manufactured by KANTO CHEMICAL CO., INC.) and RO water was added thereto. Then, an aqueous solution of 0.05 M sodium hydroxide and 1 M sodium sulfate was added so that the total volume was adjusted to 30 mL or more. The mixture was added into a centrifuge tube and stirred at room temperature for 30 minutes to carry out alkaline washing.

After the alkaline washing, the beads were washed with RO water of which volume was 20-fold of the volume of the beads on a glass filter ("11GP100" manufactured by SIBATA SCIENTIFIC TECHNOLOGY LTD.). Next, 0.5 N trisodium citrate aqueous solution prepared from trisodium citrate dihydrate (manufactured by KANTO CHEMICAL CO., INC.) and RO water of which volume was threefold of the volume of the beads was added. After it was confirmed that the filtrate became neutral, washing was carried out with RO water till the electrical conductivity of the filtrate became 1 μS/cm or lower to obtain the target adsorbent on which Protein A was immobilized. The electrical conductivity of the filtrate obtained by washing was measured using a conductivity meter ("ECTester10 Pure+" manufactured by EUTECH INSTRUMENTS).

The physical properties of the obtained adsorbent were evaluated in accordance with Test example 2. As a result, the amount of the immobilized Protein A was 35 g per 1 L of the adsorbent, and the 5% DBC of the adsorbent at RT of 3 min was 65 g per 1 L of the filling adsorbent.

Comparative Example 1

An adsorbent was prepared similarly to Example 1 except that glycerol polyglycidyl ether ("Denacol EX-314" manufactured by Nagase ChemteX Corporation) as a crosslinking agent was not added during the preparation of a cellulose dispersion. The physical properties of the obtained adsorbent were evaluated. As a result, the amount of the immobilized Protein A was 35 g per 1 L of the adsorbent, and the 5% DBC of the adsorbent at RT of 3 min was 49 g per 1 L of the filling adsorbent.

Figure 2:
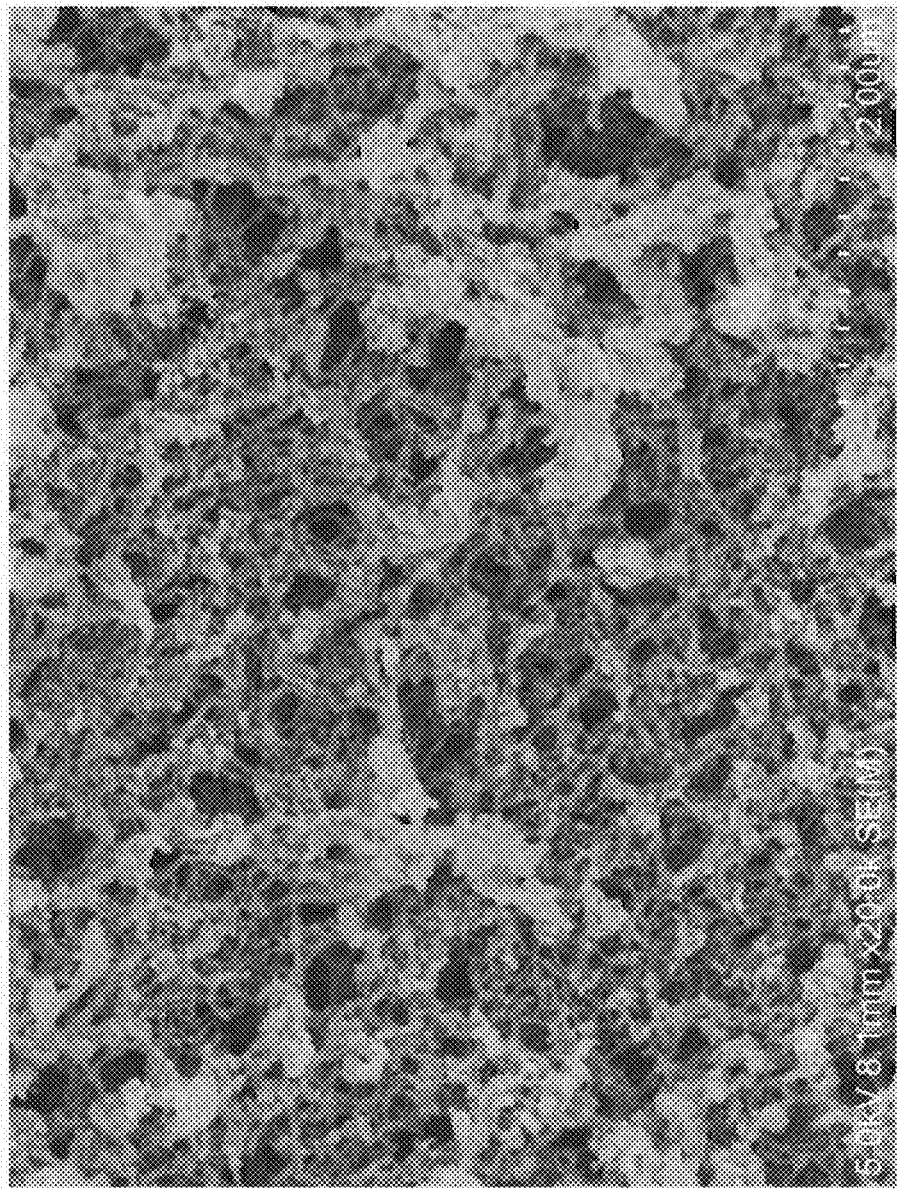
FIG. 2 is a SEM observation image of the magnified surface of the cellulose beads obtained in Comparative example 1.

The SEM observation image of the porous cellulose beads surface before Protein A was immobilized is shown as FIG. 2. When FIG. 1 and FIG. 2 are compared, it is found that surface pores of the present invention porous cellulose beads prepared by adding a crosslinking agent to a fine cellulose dispersion is apparently larger.

Example 2

(1) Preparation of Porous Cellulose Beads

Porous cellulose beads were prepared similarly to Example 1. The median diameter of the obtained porous cellulose beads was 64 μm.

(2) Classification and Crosslinking of Porous Cellulose Beads

Classification was carried out similarly to Example 1. After the liquid part of 100 mL of the classified porous cellulose beads was replaced by ethanol, the beads were added into a reaction vessel and the total amount of the cellulose beads and ethanol was adjusted to 97 g. To the mixture, 28 g of distilled water and 80 mL of epichlorohydrin were added. The temperature of the solution was adjusted to 40° C., and 96 mL of 1.8 N NaOH aqueous solution prepared from sodium hydroxide (manufactured by NACALAI TESQUE, INC.) and distilled water was added thereto to start a crosslinking reaction. After 1.5 hours from the start of the reaction, 9.6 mL of 17.0 N NaOH aqueous solution was added. In addition, after 3 hours and 4.5 hours from the start of the reaction, 9.6 mL of 17.0 N NaOH aqueous solutions were added. After 6 hours from the start of the reaction, the gel was separated and washed with distilled water of which volume was 20-fold of the volume of the beads.

Figure 4:
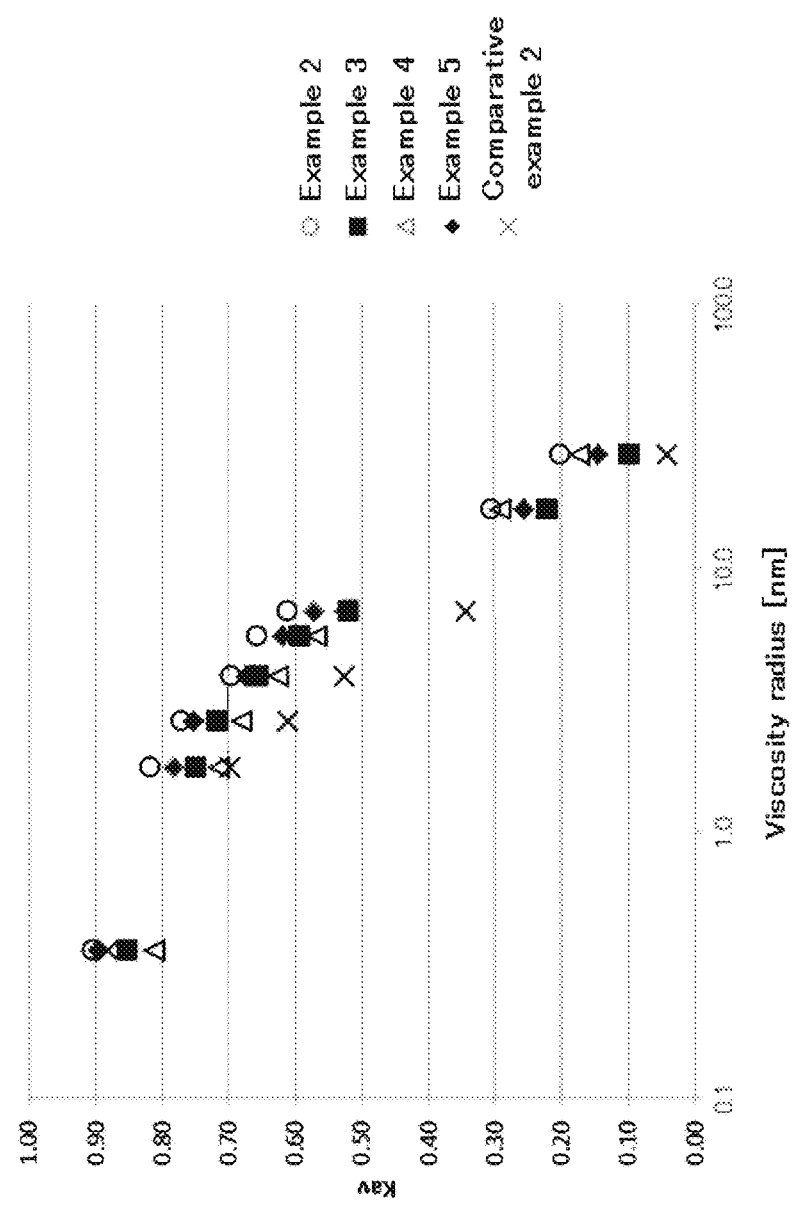
FIG. 4 is a graph which demonstrates the relation between the viscosity radius of the markers used in the measurement of $K_{av}$: gel distribution coefficient of the obtained crosslinked porous cellulose beads and the values of $K_{av}$ in Examples 2 to 5 according to the present invention and Comparative example 2.
Figure 5:
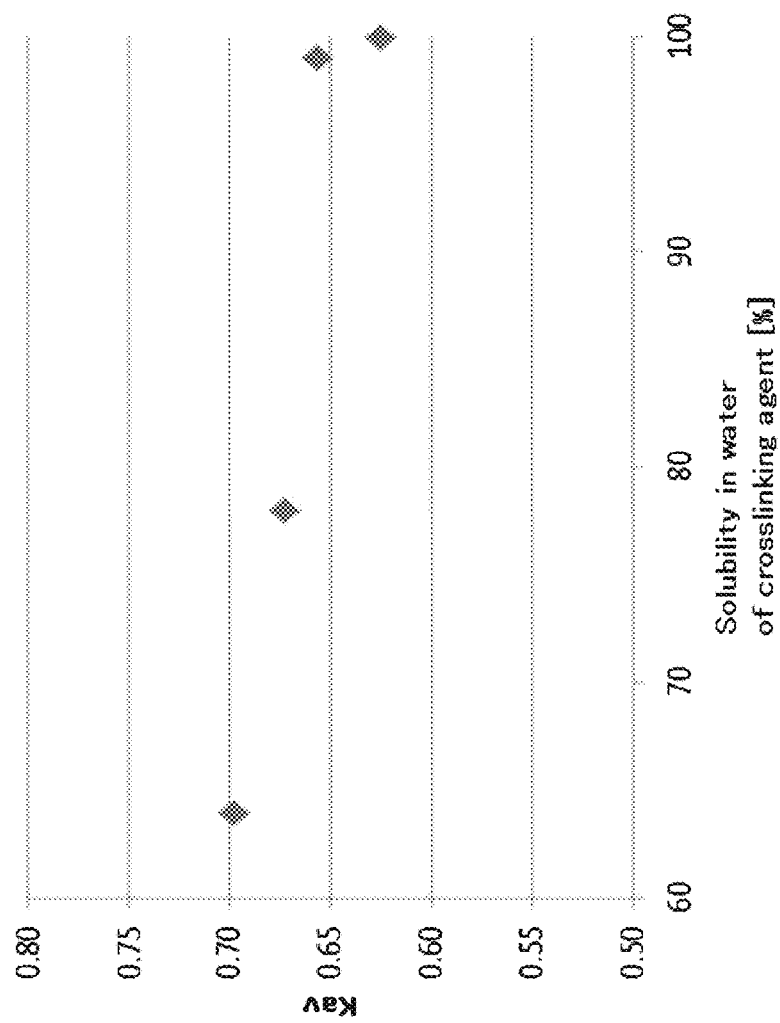
FIG. 5 is a graph which demonstrates the relation between the solubilities of the crosslinking agents added to the fine cellulose dispersions and the values of $K_{av}$ of the obtained cellulose beads.
Figure 6:
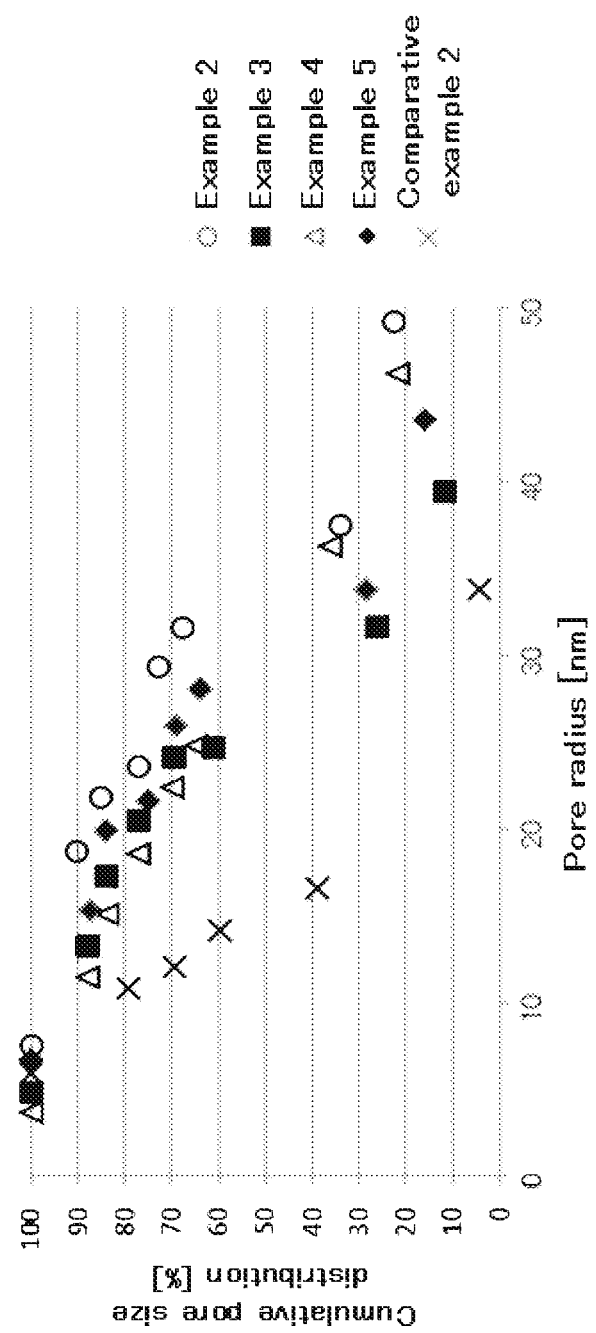
FIG. 6 is pore size distributions of the crosslinked porous cellulose beads obtained in Examples 2 to 5 according to the present invention and Comparative example 2.
Figure 7:
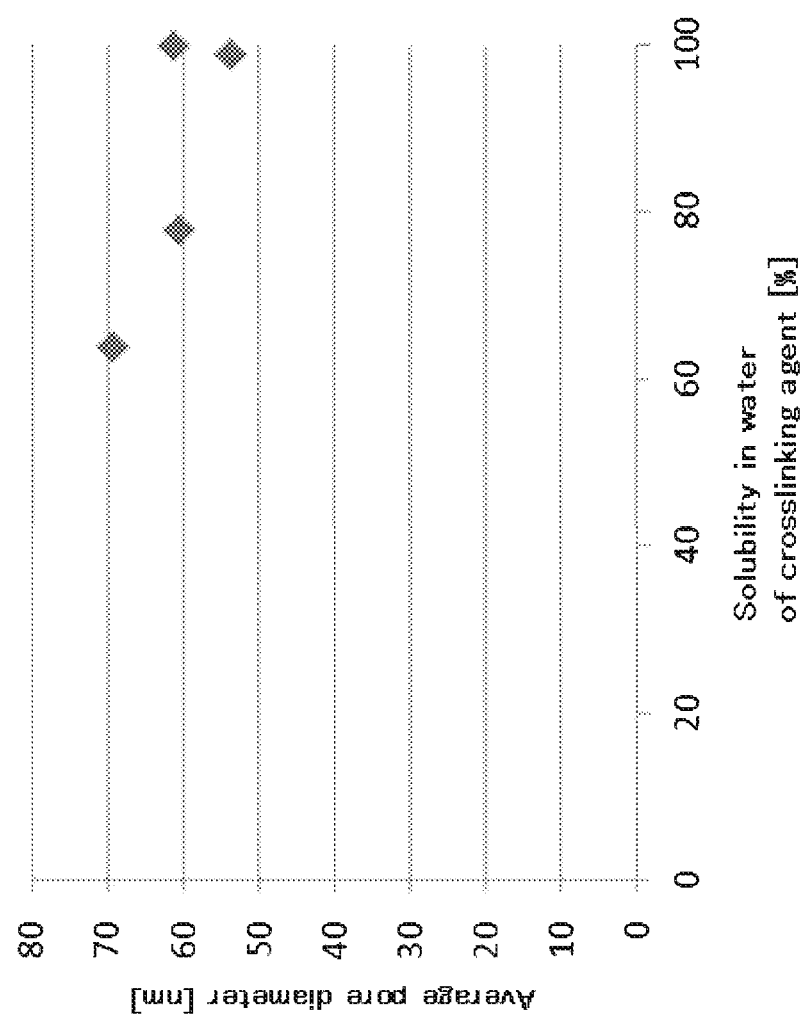
FIG. 7 is a graph which demonstrates the relation between the solubilities of the crosslinking agents added to the fine cellulose dispersions and the average pore diameter of the obtained cellulose beads.
Figure 8:
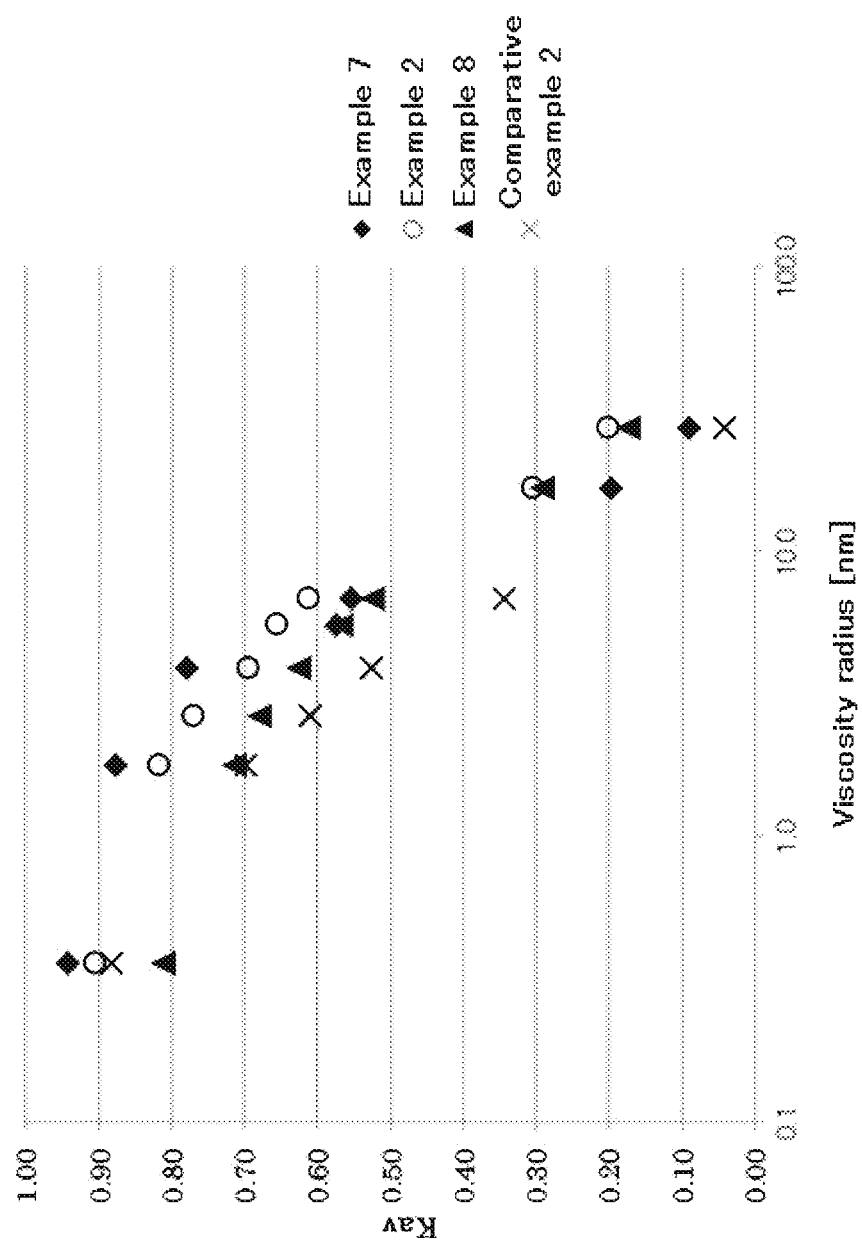
FIG. 8 is a graph which demonstrates the relation between the viscosity radius of the markers used in the measurement of $K_{av}$: gel distribution coefficient of the obtained crosslinked porous cellulose beads and the values of $K_{av}$ in Examples 2, 7 and 8 according to the present invention and Comparative example 2.

The crosslinked cellulose beads obtained by the above-described crosslinking reaction were added into a reaction vessel, and the total amount of the cellulose beads and distilled water was adjusted to 116.7 g. After 37.8 g of sodium sulfate was added thereto and dissolved, 33 mL of epichlorohydrin was added and the mixture was maintained at 40° C. To the mixture, 21 mL of 17.0 N NaOH aqueous solution was added to start a crosslinking reaction. After 2.5 hours from the start of the reaction, 5 mL of 17.0 N NaOH aqueous solution was added. After 5 hours from the start of the reaction, the gel was separated and washed with distilled water of which volume was 20-fold of the volume of the beads. The values of $K_{av}$ of the crosslinked porous cellulose beads are shown in Table 3, the relation between the viscosity radius of the used markers and the values of $K_{av}$ is shown in FIG. 4 and FIG. 8, the relation between the solubilities of the crosslinking agents in water and the values of $K_{av}$ is shown in FIG. 5, the pore size distribution and the average diameter are shown in Table 4, the pore size distribution is shown in FIG. 6 and FIG. 10, the relation between the solubilities of the crosslinking agents in water and the average pore diameter is shown in FIG. 7, the amounts of the crosslinking agents added to the fine cellulose dispersions and the values of $K_{av}$ are shown in Table 5 and FIG. 9, and the amounts of the crosslinking agents added to the fine cellulose dispersions and the average pore diameter are shown in Table 6 and FIG. 11.

Example 3

Porous cellulose beads were prepared similarly to Example 2 except that glycerol polyglycidyl ether ("Denacol EX-313" manufactured by Nagase ChemteX Corporation) was added as a crosslinking agent during the preparation of a cellulose dispersion in place of glycerol polyglycidyl ether ("EX-314" manufactured by Nagase ChemteX Corporation). The median particle diameter of the obtained porous cellulose beads was 98 μm. Then, crosslinked porous cellulose beads were prepared by carrying out classification and crosslinking similarly to Example 2 except that sieves of 38 μm and 150 μm were used. The values of $K_{av}$ of the crosslinked porous cellulose beads are shown in Table 3, the relation between the viscosity radius of the used markers and the values of $K_{av}$ is shown in FIG. 4, the relation between the solubilities of the crosslinking agents in water and the values of $K_{av}$ is shown in FIG. 5, the pore size distribution and the average pore diameter are shown in Table 4, the pore size distribution is shown in FIG. 6, and the relation between the solubilities of the crosslinking agents in water and the average pore diameter is shown in FIG. 7.

Example 4

Porous cellulose beads were prepared similarly to Example 2 except that polyglycerol polyglycidyl ether ("Denacol EX-521" manufactured by Nagase ChemteX Corporation) was added as a crosslinking agent during the preparation of a cellulose dispersion in place of glycerol polyglycidyl ether ("EX-314" manufactured by Nagase ChemteX Corporation). The median particle diameter of the obtained porous cellulose beads was 65 μm. Then, crosslinked porous cellulose beads were prepared by carrying out classification and crosslinking similarly to Example 3. The values of $K_{av}$ of the crosslinked porous cellulose beads are shown in Table 3, the relation between the viscosity radius of the used markers and the values of $K_{av}$ is shown in FIG. 4, the relation between the solubilities of the crosslinking agents in water and the values of $K_{av}$ is shown in FIG. 5, the pore size distribution and the average pore diameter are shown in Table 4, the pore size distribution is shown in FIG. 6, and the relation between the solubilities of the crosslinking agents in water and the average pore diameter is shown in FIG. 7.

Example 5

Porous cellulose beads were prepared similarly to Example 2 except that sorbitol polyglycidyl ether ("Denacol EX-614" manufactured by Nagase ChemteX Corporation) was added as a crosslinking agent during the preparation of a cellulose dispersion in place of glycerol polyglycidyl ether ("EX-314" manufactured by Nagase ChemteX Corporation). The median particle diameter of the obtained porous cellulose beads was 63 μm. Then, crosslinked porous cellulose beads were prepared by carrying out classification and crosslinking similarly to Example 3. The values of $K_{av}$ of the crosslinked porous cellulose beads are shown in Table 3, the relation between the viscosity radius of the used markers and the values of $K_{av}$ is shown in FIG. 4, the relation between the solubilities of the crosslinking agents in water and the values of $K_{av}$ is shown in FIG. 5, the pore size distribution and the average pore diameter are shown in Table 4, the pore size distribution is shown in FIG. 6, and the relation between the solubilities of the crosslinking agents in water and the average pore diameter is shown in FIG. 7.

Example 6

Porous cellulose beads were prepared similarly to Example 2 except that polypropylene glycol diglycidyl ether ("Denacol EX-920" manufactured by Nagase ChemteX Corporation) was added as a crosslinking agent during the preparation of a cellulose dispersion in place of glycerol polyglycidyl ether ("EX-314" manufactured by Nagase ChemteX Corporation). The median particle diameter of the obtained porous cellulose beads was 244 μm.

Figure 3:
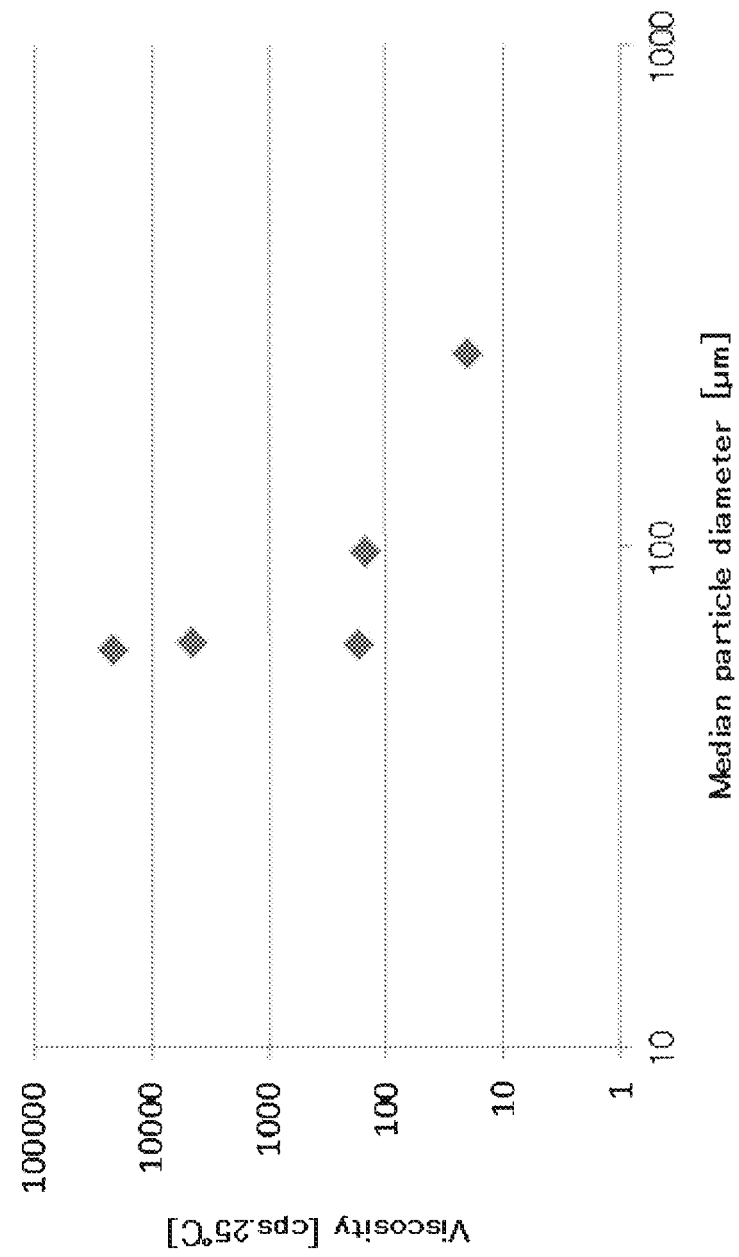
FIG. 3 is a graph which demonstrates the relation between the viscosities of the crosslinking agents added to the fine cellulose dispersions and the median diameters of the obtained cellulose beads in Examples 2 to 6 according to the present invention.

The viscosities of the crosslinking agents used in Examples 2 to 6 and the median diameters after the agglomeration are shown in Table 2 and FIG. 3.

TABLE 2

|  | Viscosity [mPa·s at 25° C.] | Median particle diameter [μm] |
|---|---|---|
| Example 2 | 170 | 64 |
| Example 3 | 150 | 98 |
| Example 4 | 4400 | 65 |
| Example 5 | 21200 | 63 |
| Example 6 | 20 | 244 |

Example 7

Porous cellulose beads were prepared similarly to Example 2 except that an amount of glycerol polyglycidyl ether ("EX-314" manufactured by Nagase ChemteX Corporation) added as a crosslinking agent during the preparation of a cellulose dispersion was adjusted to 6 g and the amount of water was increased by 6 g. Then, crosslinked porous cellulose beads were prepared by carrying out classification and crosslinking similarly to Example 3. The amounts of the crosslinking agents added to the fine cellulose dispersions and the values of $K_{av}$ are shown in Table 5 and FIG. 9, the pore size distribution is shown in FIG. 10, and the amounts of the crosslinking agents added to the fine cellulose dispersions and the average pore diameter are shown in Table 6 and FIG. 11.

Example 8

Porous cellulose beads were prepared similarly to Example 2 except that an amount of glycerol polyglycidyl ether ("EX-314" manufactured by Nagase ChemteX Corporation) added as a crosslinking agent during the preparation of a cellulose dispersion was adjusted to 18 g and the amount of water was decreased by 6 g. Then, crosslinked porous cellulose beads were prepared by carrying out classification and crosslinking similarly to Example 3. The amounts of the crosslinking agents added to the fine cellulose dispersions and the values of $K_{av}$ are shown in Table 5 and FIG. 9, the pore size distribution is shown in FIG. 10, and the amounts of the crosslinking agents added to the fine cellulose dispersions and the average pore diameter are shown in Table 6 and FIG. 11.

Comparative Example 2

Porous cellulose beads were prepared similarly to Example 2 except that glycerol polyglycidyl ether ("EX-314" manufactured by Nagase ChemteX Corporation) was not added as a crosslinking agent during the preparation of a cellulose dispersion and the amount of water was increased by 12 g. Then, crosslinked porous cellulose beads were prepared by carrying out classification and crosslinking similarly to Example 3. The values of $K_{av}$ of the crosslinked porous cellulose beads are shown in Table 3, the relation between the viscosity radius of the used markers and the values of $K_{av}$ is shown in FIG. 4 and FIG. 8, the relation between the solubilities of the crosslinking agents in water and the values of $K_{av}$ is shown in FIG. 5, the pore size distribution and the average pore diameter are shown in Table 4, the pore size distribution is shown in FIG. 6 and FIG. 10, the relation between the solubilities of the crosslinking agents in water and the average pore diameter is shown in FIG. 7, the amounts of the crosslinking agents added to the fine cellulose dispersions and the values of $K_{av}$ are shown in Table 5 and FIG. 9, and the amounts of the crosslinking agents added to the fine cellulose dispersions and the average pore diameter are shown in Table 6 and FIG. 11.

TABLE 3

|  | | Example 2 | Example 3 | Example 4 | Example 5 | Comparative example 2 |
|---|---|---|---|---|---|---|
| Crosslinking agent | | EX314 | EX313 | EX521 | EX614 | — |
| Solubility of crosslinking agent in water [%] | | 64 | 99 | 100 | 78 | — |
| Viscosity of crosslinking agent [mPa · s 25° C.] | | 170 | 150 | 4400 | 21200 | — |
| Marker | | | | | | |
| Molecular weight | Viscosity radius [nm] | $K_{av}$ | $K_{av}$ | $K_{av}$ | $K_{av}$ | $K_{av}$ |
| 1185000 | 27.0 | 0.20 | 0.10 | 0.17 | 0.14 | 0.04 |
| 667800 | 16.7 | 0.31 | 0.22 | 0.29 | 0.26 | |
| 80900 | 6.8 | 0.61 | 0.52 | 0.52 | 0.57 | 0.34 |
| 48600 | 5.5 | 0.66 | 0.59 | 0.57 | 0.62 | |
| 23800 | 3.9 | 0.70 | 0.66 | 0.63 | 0.67 | 0.53 |
| 11600 | 2.6 | 0.77 | 0.72 | 0.68 | 0.75 | 0.61 |
| 5250 | 1.8 | 0.82 | 0.75 | 0.71 | 0.78 | 0.70 |
| 180 | 0.4 | 0.91 | 0.85 | 0.81 | 0.90 | 0.88 |

As the results shown in Table 3 and FIG. 4, it was demonstrated that the values of $K_{av}$, in other words, pore volume in cellulose beads, can be increased by adding a crosslinking agent to a fine cellulose dispersion for agglomeration.

In addition, as the results shown in Table 3 and FIG. 5, it was found that when a crosslinking agent having high solubility in water is used for adding to a fine cellulose dispersion, the volume of the pores suitable for the marker having viscosity radius of 3.9 nm, which is approximately the size of an antibody, is large.

TABLE 4

|  | Example 2 | Example 3 | Example 4 | Example 5 | Comparative example 2 |
|---|---|---|---|---|---|
| Crosslinking agent | EX314 | EX313 | EX521 | EX614 | — |
| Solubility of crosslinking agent in water [%] | 64 | 99 | 100 | 78 | — |
| Viscosity of crosslinking agent [mPa · s 25° C.] | 170 | 150 | 4400 | 21200 | — |
| Average pore diameter of beads [nm] | 69 | 54 | 61 | 61 | 30 |

| Molecular weight of marker | Pore radius [nm] | Cumulative pore size distribution [%] | Pore radius [nm] | Cumulative pore size distribution [%] | Pore radius [nm] | Cumulative pore size distribution [%] | Pore radius [nm] | Cumulative pore size distribution [%] | Pore radius [nm] | Cumulative pore size distribution [%] |
|---|---|---|---|---|---|---|---|---|---|---|
| 1185000 | 49 | 23 | 39 | 12 | 46 | 22 | 44 | 16 | 34 | 4 |
| 667800 | 37 | 34 | 32 | 26 | 36 | 36 | 34 | 28 | | |
| 80900 | 32 | 68 | 25 | 61 | 25 | 65 | 28 | 64 | 17 | 39 |
| 48600 | 29 | 73 | 24 | 70 | 22 | 70 | 26 | 69 | 20 | |
| 23800 | 24 | 77 | 20 | 77 | 19 | 77 | 22 | 75 | 14 | 59 |
| 11600 | 22 | 85 | 17 | 84 | 15 | 84 | 20 | 84 | 12 | 69 |

TABLE 4-continued

|  | Example 2 | | Example 3 | | Example 4 | | Example 5 | | Comparative example 2 | |
| --- | --- | --- | --- | --- | --- | --- | --- | --- | --- | --- |
| 5250 | 19 | 90 | 13 | 88 | 11 | 88 | 15 | 87 | 11 | 79 |
| 180 | 7 | 100 | 5 | 100 | 4 | 100 | 7 | 100 | 6 | 100 |

As the results shown in Table 4 and FIG. 6, it was demonstrated that pore is remarkably increased by adding a crosslinking agent to a fine cellulose dispersion for agglomeration.

In addition, as the results shown in Table 4 and FIG. 7, it was found that when a crosslinking agent having high solubility in water is used for adding to a fine cellulose dispersion, the radius of the pores develops into an appropriate size.

TABLE 5

|  | Comparative example 2 | Example 7 | Example 2 | Example 8 |
| --- | --- | --- | --- | --- |
| Crosslinking agent | — | EX314 | EX314 | EX521 |
| Amount of added crosslinking agent [%] | 0 | 5 | 10 | 15 |

| Marker | | | | | |
| --- | --- | --- | --- | --- | --- |
| Molecular weight | Viscosity radius [nm] | $K_{av}$ | $K_{av}$ | $K_{av}$ | $K_{av}$ |
| 1185000 | 27.0 | 0.04 | 0.09 | 0.20 | 0.17 |
| 667800 | 16.7 |  | 0.20 | 0.31 | 0.29 |
| 80900 | 6.8 | 0.34 | 0.55 | 0.61 | 0.52 |
| 48600 | 5.5 |  | 0.57 | 0.66 | 0.57 |
| 23800 | 3.9 | 0.53 | 0.78 | 0.70 | 0.63 |
| 11600 | 2.6 | 0.61 |  | 0.77 | 0.68 |
| 5250 | 1.8 | 0.70 | 0.88 | 0.82 | 0.71 |
| 180 | 0.4 | 0.88 | 0.94 | 0.91 | 0.81 |

As the results shown in Table 5 and FIG. 8, it was demonstrated that the values of $K_{av}$, in other words, pore volume in cellulose beads, can be increased by adding a crosslinking agent to a fine cellulose dispersion for agglomeration.

Figure 9:
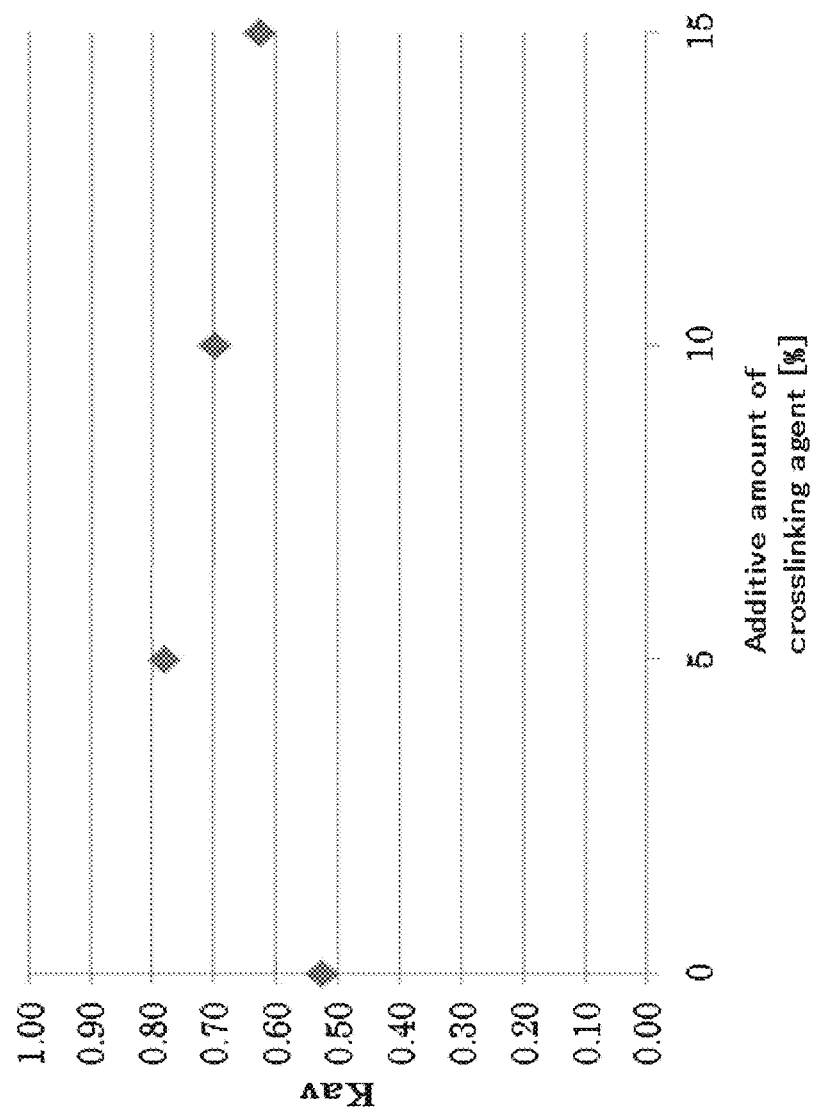
FIG. 9 is a graph which demonstrates the relation between the amounts of the crosslinking agents added to the fine cellulose dispersions and the values of $K_{av}$ of the obtained cellulose beads.
Figure 10:
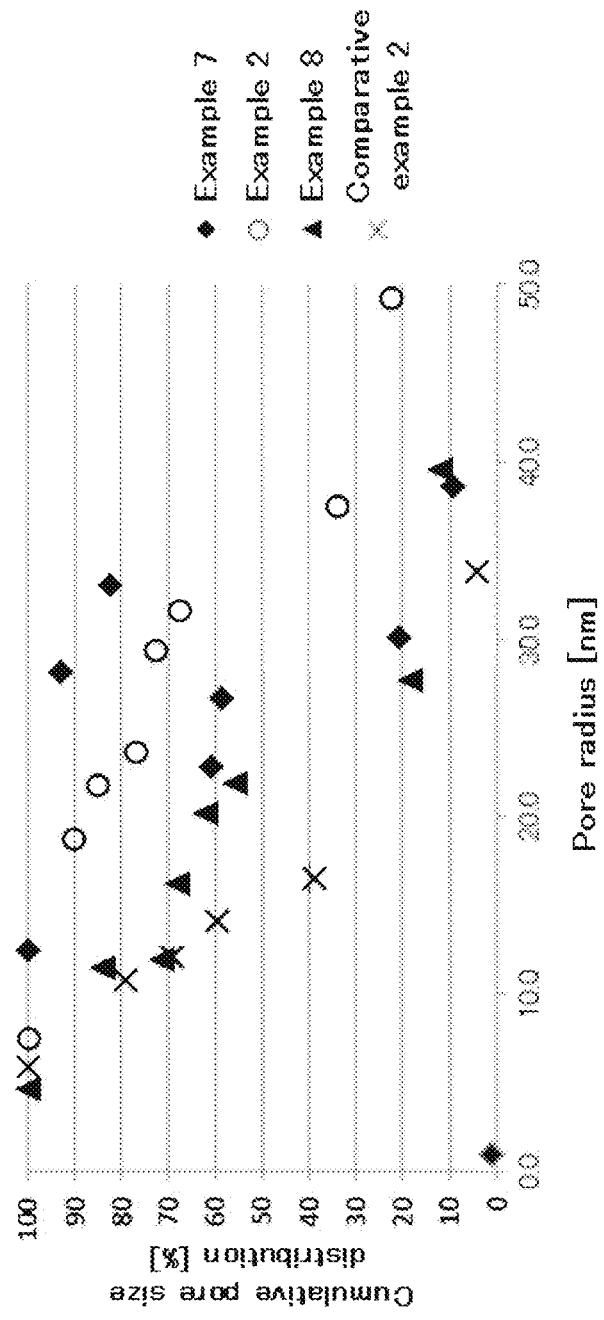
FIG. 10 is pore size distributions of the crosslinked porous cellulose beads obtained in Examples 2, 7 and 8 according to the present invention and Comparative example 2.

In addition, as the results shown in Table 5 and FIG. 9, it was found that when an amount of a crosslinking agent in a mixed liquid of a fine cellulose dispersion and the crosslinking agent is 5%, the volume of the pores suitable for the marker having viscosity radius of 3.9 nm, which is approximately the size of an antibody, is large.

TABLE 6

|  | Comparative example 2 | Example 7 | Example 2 | Example 8 |
| --- | --- | --- | --- | --- |
| Crosslinking agent | — | EX314 | EX314 | EX314 |
| Amount of added crosslinking agent [%] | 0 | 5 | 10 | 15 |
| Average pore diameter of beads [nm] | 30 | 55 | 69 | 45 |

| Molecular weight of marker | Pore radius [nm] | Cumulative pore size distribution [%] | Pore radius [nm] | Cumulative pore size distribution [%] | Pore radius [nm] | Cumulative pore size distribution [%] | Pore radius [nm] | Cumulative pore size distribution [%] |
| --- | --- | --- | --- | --- | --- | --- | --- | --- |
| 1185000 | 34 | 4 | 38.6 | 9 | 49 | 23 | 39.6 | 12 |
| 667800 |  |  | 30.1 | 21 | 37 | 34 | 27.7 | 18 |
| 80900 | 17 | 39 | 26.7 | 59 | 32 | 68 | 21.9 | 56 |
| 48600 | 20 |  | 22.8 | 61 | 29 | 73 | 20.2 | 62 |
| 23800 | 14 | 59 | 33.0 | 83 | 24 | 77 | 16.2 | 68 |
| 11600 | 12 | 69 | 45.6 |  | 22 | 85 | 12.0 | 71 |
| 5250 | 11 | 79 | 28.1 | 93 | 19 | 90 | 11.5 | 84 |
| 180 | 6 | 100 | 12.5 | 100 | 7 | 100 | 4.6 | 100 |

Figure 11:
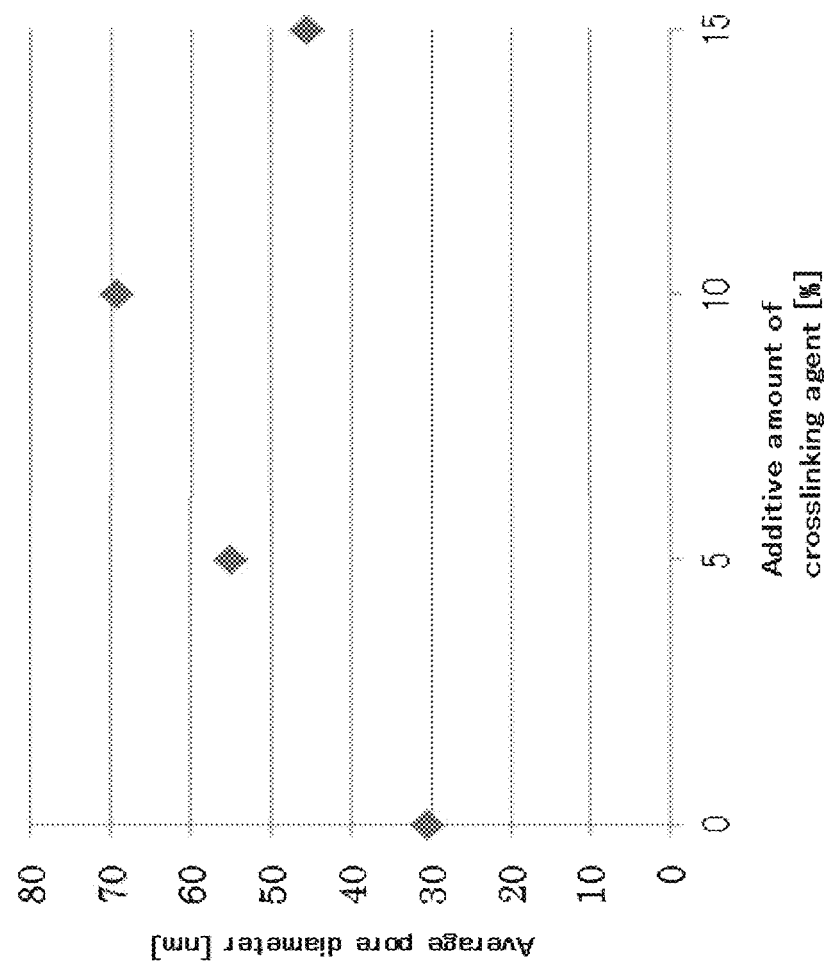
FIG. 11 is a graph which demonstrates the relation between the amounts of the crosslinking agents added to the fine cellulose dispersions and the average pore diameter of the obtained cellulose beads.

As the results shown in Table 6, FIG. 10 and FIG. 11, when an amount of a crosslinking agent in a mixed liquid of a fine cellulose dispersion and the crosslinking agent was 10%, the average pore diameter was the largest.

Example 9

Crosslinked porous beads were prepared similarly to Example 2 and subjected to wet classification using sieves of 38 μm and 90 μm to adjust the median particle diameter to 65 μm.

Into a centrifuge tube, 3.5 mL of the obtained crosslinked beads were added. RO water was added thereto to adjust the total amount to 6 mL. The centrifuge tube was set on a mix rotor ("MIX ROTOR MR-3" manufactured by AS ONE Corporation) to stir the mixture. Then, 2.0 mL of 11.16 mg/mL sodium periodate aqueous solution was prepared by dissolving sodium periodate in RO water, and was added into the centrifuge tube. The mixture was stirred at 25° C. for 1 hour. After the reaction, the beads were washed with RO water on a glass filter ("11GP100" manufactured by SIBATA SCIENTIFIC TECHNOLOGY LTD.) till the electrical conductivity of the filtrate became 1 μS/cm or lower to obtain formyl group-containing crosslinked porous cellulose beads. The electrical conductivity of the filtrate obtained by washing was measured using a conductivity meter ("ECTester10 Pure+" manufactured by EUTECH INSTRUMENTS).

Into a centrifuge tube, 3.5 mL of the obtained formyl group-containing crosslinked porous cellulose beads were added. RO water was added thereto to adjust the total amount to 7.5 mL. Into the centrifuge tube, 1.91 g of 64 mg/mL aqueous solution of the orientation-controlled alkali-resistant Protein A produced in Production example 2 was added. Then, the mixture was stirred at 6° C. for 2 hours. Next, 1.61 mL of 1.5 M trisodium citrate aqueous solution was added thereto, and the pH value of the mixture was adjusted to 12 using 0.08 N sodium hydroxide aqueous solution. The mixture was stirred at 6° C. for 23 hours using a mixing rotor ("MIX ROTOR MR-3" manufactured by AS ONE Corporation) for the reaction.

Then, filtration was carried out using a glass filter to obtain a filtrate. Hereinafter, the filtrate is referred to as "Reaction mixture 1". The liquid part contained in the beads was replaced by a buffer of which pH was adjusted to 5 using 0.1 M trisodium citrate aqueous solution in RO water and 0.1 M citric acid aqueous solution. Then, the beads were added into a centrifuge tube again with adjusting the total volume to 7 mL with the same buffer. The mixture was stirred at 6° C. for 4 hours using a mixing rotor ("MIX ROTOR MR-3" manufactured by AS ONE Corporation). Subsequently, 1.93 mL of 5.5 mass % dimethylamine borane aqueous solution in RO water was added thereto, and the mixture was stirred at 6° C. for 1 hour. Then, the reaction temperature was increased to 25° C., and the reaction was carried out at 25° C. for 18 hours with stirring by a mixing rotor ("MIX ROTOR MR-3" manufactured by AS ONE Corporation). After the reaction, the reaction mixture was separated. Hereinafter, the reaction mixture is referred to as "Reaction mixture 2". The amount of the immobilized Protein A was determined by measuring UV absorbance of absorption maximum at about 278 nm of Reaction mixture 1 and Reaction mixture 2, and subtracting the measured amount value from the used ligand amount.

The beads after the reaction was washed with RO water of which volume was threefold of the volume of the beads on a glass filter ("11GP100" manufactured by SIBATA SCIENTIFIC TECHNOLOGY LTD.). Then, threefold volume amount of 0.1 N citric acid aqueous solution in RO water was added to the beads, and 0.1 N citric acid aqueous solution in RO water was further added thereto so that the total volume was adjusted to 30 mL or more. The mixture was added into a centrifuge tube and stirred at 25° C. for 30 minutes to carry out acid washing.

After the acid washing, the beads were washed with RO water of which volume was threefold of the volume of the beads on a glass filter ("11GP100" manufactured by SIBATA SCIENTIFIC TECHNOLOGY LTD.). Next, threefold volume of an aqueous solution of 0.05 M sodium hydroxide and 1 M sodium sulfate in RO water was added thereto. Then, an aqueous solution of 0.05 M sodium hydroxide and 1 M sodium sulfate was added so that the total volume was adjusted to 30 mL or more. The mixture was added into a centrifuge tube and stirred at room temperature for 30 minutes to carry out alkaline washing.

After the alkaline washing, the beads were washed with RO water of which volume was 20-fold of the volume of the beads on a glass filter ("11GP100" manufactured by SIBATA SCIENTIFIC TECHNOLOGY LTD.). Next, 0.1 N trisodium citrate aqueous solution in RO water of which volume was threefold of the volume of the beads was added. After it was confirmed that the filtrate became neutral, washing was carried out with RO water till the electrical conductivity of the filtrate became 1 μS/cm or lower to obtain the target adsorbent on which orientation-controlled alkali-resistant Protein A was immobilized. The electrical conductivity of the filtrate obtained by washing was measured using a conductivity meter ("ECTester10 Pure+" manufactured by EUTECH INSTRUMENTS).

Figure 13:
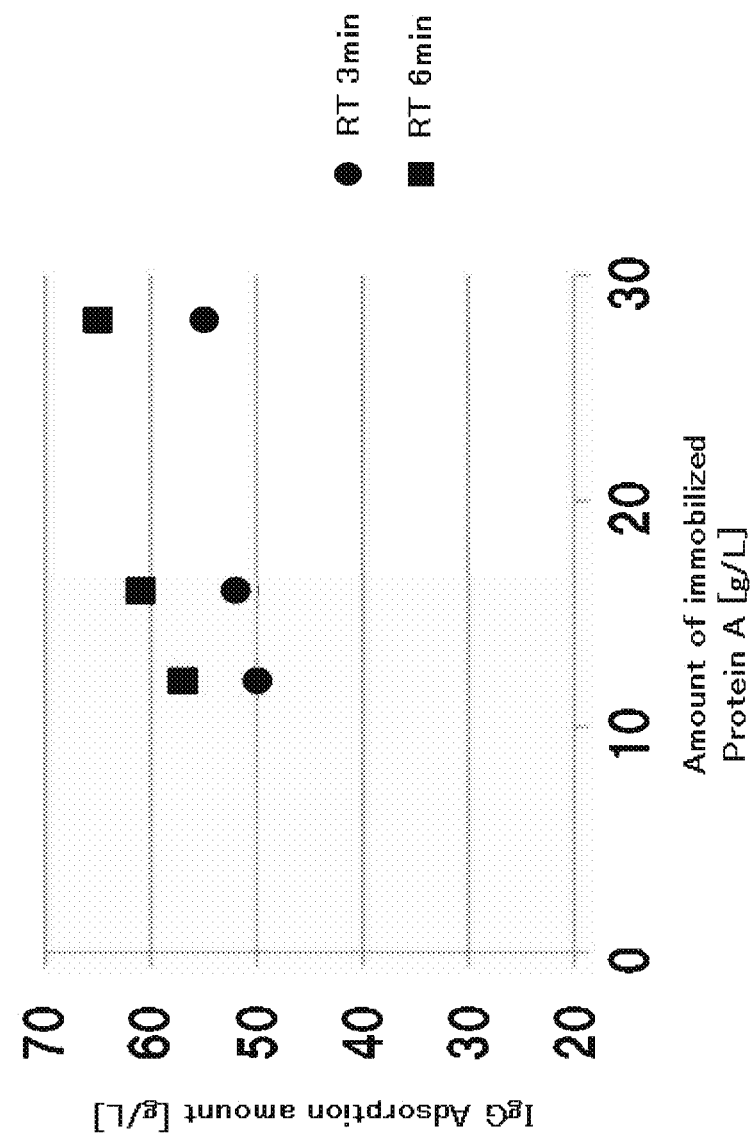
FIG. 13 is a graph which demonstrates the relation between the amounts of the immobilized Protein A and IgG adsorption amounts of the adsorbent.
Figure 14:
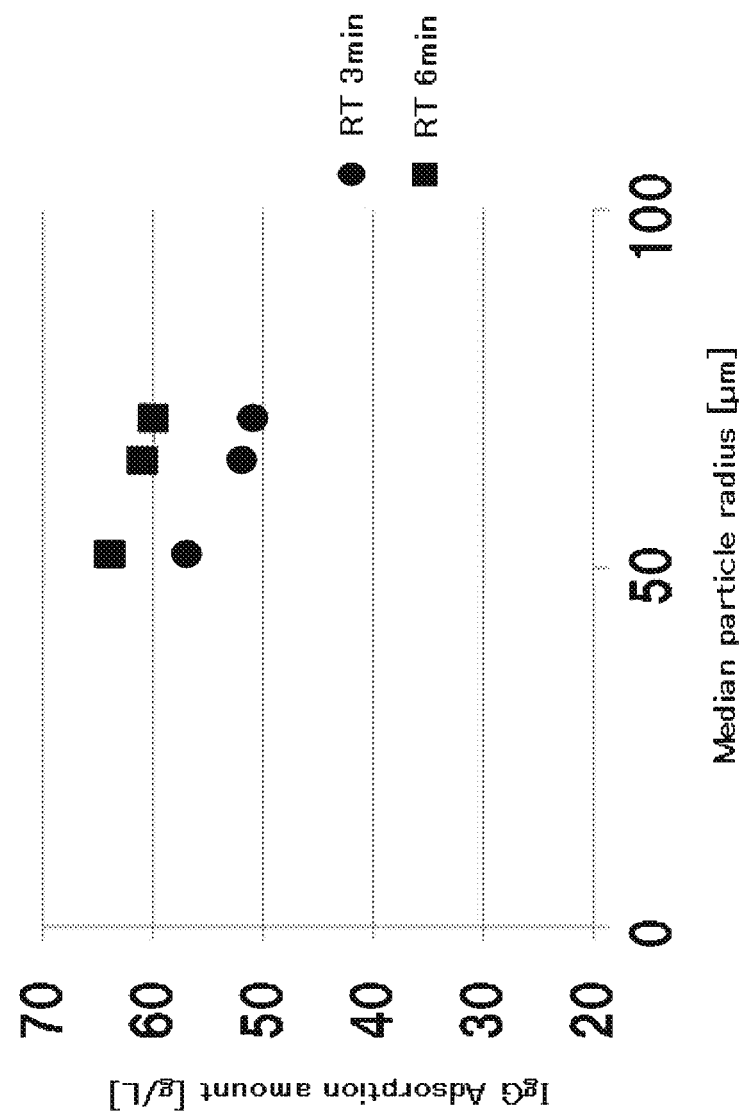
FIG. 14 is a graph which demonstrates the relation between the median particle diameters and IgG adsorption amounts of the adsorbent.

With respect to the obtained adsorbent, adsorption performance for IgG was measured in accordance with Test example 3 and 20% compression stress was measured in accordance with Test example 4. The adsorption performance and 20% compression stress are shown in Table 7, the relation between the amounts of the immobilized Protein A and IgG adsorption amounts is shown in FIG. 13, and the relation between the median particle diameters and IgG adsorption amounts is shown in FIG. 14.

Example 10

An adsorbent was prepared similarly to the Example 9 except that the amount of the orientation-controlled alkali-resistant Protein A aqueous solution was changed to 1.10 g.

With respect to the obtained adsorbent, adsorption performance for IgG was measured in accordance with Test example 3 and 20% compression stress was measured in accordance with Test example 4. The adsorption performance and 20% compression stress are shown in Table 7, the relation between the amounts of the immobilized Protein A and IgG adsorption amounts is shown in FIG. 13, and the relation between the median particle diameters and IgG adsorption amounts is shown in FIG. 14.

Example 11

An adsorbent was prepared similarly to Example 9 except that the amount of the orientation-controlled alkali-resistant Protein A aqueous solution was changed to 0.82 g.

With respect to the obtained adsorbent, adsorption performance for IgG was measured in accordance with Test example 3 and 20% compression stress was measured in accordance with Test example 4. The adsorption performance and 20% compression stress are shown in Table 7, the relation between the amounts of the immobilized Protein A and IgG adsorption amounts is shown in FIG. 13, and the relation between the median particle diameters and IgG adsorption amounts is shown in FIG. 14.

Example 12

An adsorbent was prepared similarly to Example 10 except that the crosslinked porous cellulose beads were subjected to wet classification using sieves of 38 μm and 63 μm, and the obtained crosslinked porous cellulose beads having a median particle diameter of 52 μm were used.

Figure 12:
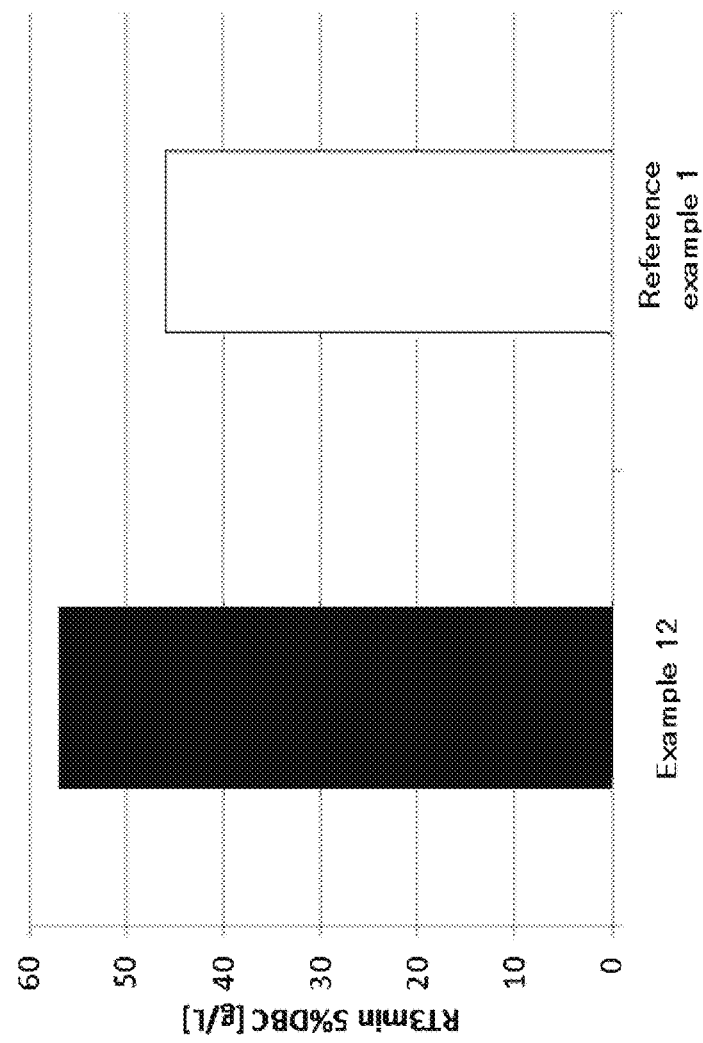
FIG. 12 is a graph to compare the adsorption performance between the adsorbents of Example 12 according to the present invention and Reference example 1.

With respect to the obtained adsorbent, adsorption performance for IgG was measured in accordance with Test example 3 and 20% compression stress was measured in accordance with Test example 4. The adsorption performance and 20% compression stress are shown in Table 7, and the result to compare the adsorption performance with Reference example 1 is shown in FIG. 12.

Example 13

An adsorbent was prepared similarly to Example 10 except that the crosslinked porous cellulose beads were subjected to wet classification using sieves of 63 μm and 75 μm, and the obtained crosslinked porous cellulose beads having a median particle diameter of 71 μm were used.

With respect to the obtained adsorbent, adsorption performance for IgG was measured in accordance with Test example 3 and 20% compression stress was measured in accordance with Test example 4. The adsorption performance and 20% compression stress are shown in Table 7.

Reference Example 1

With respect to the high performance adsorbent for purifying antibody pharmaceutical, "MabSelect SuRe LX" manufactured by GE Healthcare Corporation, on which alkali-resistant Protein A was immobilized, adsorption performance was measured in accordance with Test example 3 and 20% compression stress was measured in accordance with Test example 4. The adsorption performance is shown in Table 7, and the result to compare the adsorption performance with Example 12 is shown in FIG. 12.

TABLE 7

|  | RT3 min 5% DBC [g/L] | RT6 min 5% DBC [g/L] | 20% compression stress [MPa] | Median diameter [μm] | Amount of immobilized PA [g/L] |
| --- | --- | --- | --- | --- | --- |
| Example 9 | 55 | 65 | 0.13 | 65 | 28 |
| Example 10 | 52 | 61 | 0.13 | 65 | 16 |
| Example 11 | 50 | 57 | 0.13 | 65 | 12 |
| Example 12 | 57 | 64 | 0.12 | 52 | 15 |
| Example 13 | 51 | 60 | 0.12 | 71 | 16 |
| Reference example 1 | 46 | 63 | 0.12 | 85 | — |

As the results shown in Table 7 and FIG. 12, the adsorbent according to the present invention exhibits very excellent adsorption performance in comparison with the conventionally-known adsorbent product. In addition, as the result shown in FIG. 13, with respect to the adsorbent according to the present invention, it was demonstrated that even when the amount of immobilized ligand is small, the adsorption performance is less likely to be decreased. Furthermore, as the result shown in FIG. 14, with respect to the adsorbent according to the present invention, it was found that even when the median particle diameter is large, the adsorption performance is less likely to be decreased. In other words, it was demonstrated that the porous cellulose beads according to the present invention are good at mass transfer, and a very high performance adsorbent on which a target substance can be adsorbed with high efficiency can be obtained by immobilizing a ligand on the porous cellulose beads.

The invention claimed is:

1. A method for producing porous cellulose beads, the method comprising:
   mixing an alkaline aqueous solution having a temperature of not less than −20° C. and not more than 20° C. and cellulose to obtain a cellulose dispersion;
   adding a crosslinking agent to the cellulose dispersion to obtain a mixed liquid;
   dispersing the mixed liquid in a dispersion medium to obtain an emulsion; and
   contacting the emulsion with a coagulating solvent.

2. The method according to claim 1, wherein, in the mixing, the temperature of the alkaline aqueous solution is not less than 0° C. and not more than 20° C.

3. The method according to claim 1, wherein the crosslinking agent is an epoxy group-containing compound.

4. The method according to claim 3, wherein the epoxy group-containing compound is a glycidyl ether compound.

5. The method according to claim 1, wherein the crosslinking agent has a solubility in water of not less than 50%.

6. The method according to claim 1, wherein a viscosity of the crosslinking agent is not less than 100 mPa·s and not more than 50,000 mPa·s.

7. The method according to claim 1, wherein, in the mixing, the temperature of the alkaline aqueous solution is not less than −20° C. and not more than 15° C.

8. The method according to claim 1, wherein a concentration of the crosslinking agent in the mixed liquid is from 1 wt % to 20 wt %.

9. The method according to claim 1, wherein an alkali concentration of the alkaline aqueous solution is from 3 wt % to 20 wt %.

10. The method according to claim 1, wherein the cellulose has a polymerization degree of not more than 1,000.

11. The method according to claim 1, wherein a concentration of the cellulose in the cellulose dispersion is from 1 wt % to 20 wt %.

* * * * *

SEQUENCE LISTING

<160> NUMBER OF SEQ ID NOS: 2

<210> SEQ ID NO 1
<211> LENGTH: 291
<212> TYPE: PRT
<213> ORGANISM: Staphylococcus aureus

<400> SEQUENCE: 1

```
Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Lys Phe
    50                  55                  60

Asn Lys Asp Gln Gln Ser Ala Phe Tyr Glu Ile Leu Asn Met Pro Asn
65                  70                  75                  80

Leu Asn Glu Glu Gln Arg Asn Gly Phe Ile Gln Ser Leu Lys Asp Asp
```

-continued

```
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ala Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 2
<211> LENGTH: 290
<212> TYPE: PRT
<213> ORGANISM: Artificial Sequence
<220> FEATURE:
<223> OTHER INFORMATION: PA mutant

<400> SEQUENCE: 2

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Arg Leu Arg Asp Asp Pro Ser Val Ser Arg Glu Ile Leu Ala Glu Ala
        35                  40                  45

Gln Arg Leu Asn Asp Ala Gln Ala Pro Lys Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Arg Leu Arg Asp Asp Pro
                85                  90                  95

Ser Val Ser Arg Glu Ile Leu Ala Glu Ala Gln Arg Leu Asn Asp Ala
            100                 105                 110

Gln Ala Pro Lys Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Arg Leu Arg Asp Asp Pro Ser Val Ser Arg Glu Ile
```

```
                145                 150                 155                 160
Leu Ala Glu Ala Gln Arg Leu Asn Asp Ala Gln Ala Pro Lys Ala Asp
                    165                 170                 175

Asn Arg Phe Asn Arg Glu Gln Gln Asn Ala Phe Tyr Glu Ile Leu His
                180                 185                 190

Leu Pro Asn Leu Thr Glu Glu Gln Arg Asn Ala Phe Ile Gln Arg Leu
        195                 200                 205

Arg Asp Asp Pro Ser Val Ser Arg Glu Ile Leu Ala Glu Ala Gln Arg
    210                 215                 220

Leu Asn Asp Ala Gln Ala Pro Lys Ala Asp Asn Arg Phe Asn Arg Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Arg Leu Arg Asp Asp Pro Ser Val
            260                 265                 270

Ser Arg Glu Ile Leu Ala Glu Ala Gln Arg Leu Asn Asp Ala Gln Ala
        275                 280                 285

Pro Lys
    290
```